(12) United States Patent
Mehl et al.

(10) Patent No.: US 8,816,001 B2
(45) Date of Patent: Aug. 26, 2014

(54) GENETICALLY ENCODED INITIATOR FOR POLYMER GROWTH FROM PROTEINS

(71) Applicant: Franklin and Marshall College, Lancaster, PA (US)

(72) Inventors: Ryan A. Mehl, Corvallis, OR (US); Krzysztof Matyjaszewski, Pittsburgh, PA (US); Saadyah Averick, Pittsburgh, PA (US)

(73) Assignee: Franklin and Marshall College, Lancaster, PA (US)

( * ) Notice: Subject to any disclaimer, the term of this patent is extended or adjusted under 35 U.S.C. 154(b) by 0 days.

(21) Appl. No.: 13/788,710

(22) Filed: Mar. 7, 2013

(65) Prior Publication Data

US 2013/0261259 A1    Oct. 3, 2013

Related U.S. Application Data

(63) Continuation of application No. PCT/US2011/051043, filed on Sep. 9, 2011.

(60) Provisional application No. 61/381,757, filed on Sep. 10, 2010.

(51) Int. Cl.
| | |
|---|---|
| A61K 47/48 | (2006.01) |
| C07C 229/00 | (2006.01) |
| C07C 69/00 | (2006.01) |
| C07C 69/63 | (2006.01) |
| C07C 247/00 | (2006.01) |
| C07K 1/00 | (2006.01) |

(52) U.S. Cl.
USPC .......... 525/54.1; 562/449; 560/228; 560/142; 552/10; 552/12; 530/350; 435/68.1

(58) Field of Classification Search
USPC ................. 525/54.1; 562/449; 560/228, 142; 552/10, 12; 530/350; 435/68.1
See application file for complete search history.

(56) References Cited

U.S. PATENT DOCUMENTS

| | | |
|---|---|---|
| 4,033,998 A | 7/1977 | Harris |
| 5,763,546 A | 6/1998 | Jung et al. |

(Continued)

FOREIGN PATENT DOCUMENTS

| | | |
|---|---|---|
| WO | 2004087777 A2 | 10/2004 |
| WO | 2005087818 A1 | 9/2005 |

(Continued)

OTHER PUBLICATIONS

STN structure search, (p. 8) Hamamoto et al., [Peptide Science (2010), 47th, 113].*

(Continued)

*Primary Examiner* — William Cheung
(74) *Attorney, Agent, or Firm* — Barley Snyder

(57) ABSTRACT

This invention pertains to methods for producing homogeneous recombinant proteins that contain polymer initiators at defined sites. The unnatural amino acid, 4-(2'-bromoisobutyramido)phenylalanine of formula 1, was designed and synthesized as a molecule comprising a functional group further comprising an initiator for an atom-transfer radical polymerization ('ATRP') that additionally would provide a stable linkage between the protein and growing polymer. We evolved a *Methanococcus jannaschii* (Mj) tyrosyl-tRNA synthetase/tRNA$_{CUA}$ pair to genetically encode this unnatural amino acid in response to an amber codon. To demonstrate the utility of this functional amino acid, we produced Green Fluorescent Protein with the unnatural amino acid initiator of formula 1 site-specifically incorporated on its surface (GFP-1). Purified GFP-1 was then used as an initiator under standard ATRP conditions with oligo(ethylene oxide)monomethyl ether methacrylate, efficiently producing a polymer-GFP bioconjugate wherein the polymer is connected at a specifically selected site on GFP.

21 Claims, 8 Drawing Sheets

(56) References Cited

U.S. PATENT DOCUMENTS

| | | | |
|---|---|---|---|
| 5,789,487 | A | 8/1998 | Matyjaszewski et al. |
| 5,807,937 | A | 9/1998 | Matyjaszewski et al. |
| 5,945,491 | A | 8/1999 | Matyjaszewski et al. |
| 6,111,022 | A | 8/2000 | Matyjaszewski et al. |
| 6,121,371 | A | 9/2000 | Matyjaszewski et al. |
| 6,124,411 | A | 9/2000 | Matyjaszewski et al. |
| 6,162,882 | A | 12/2000 | Matyjaszewski et al. |
| 6,197,794 | B1 | 3/2001 | Head et al. |
| 6,407,187 | B1 | 6/2002 | Matyjaszewski et al. |
| 6,492,421 | B1 | 12/2002 | Thorsett et al. |
| 6,512,060 | B1 | 1/2003 | Matyjaszewski et al. |
| 6,538,091 | B1 | 3/2003 | Matyjaszewski et al. |
| 6,541,580 | B1 | 4/2003 | Matyjaszewski et al. |
| 6,624,262 | B2 | 9/2003 | Matyjaszewski et al. |
| 6,627,314 | B2 | 9/2003 | Matyjaszewski et al. |
| 6,759,491 | B2 | 7/2004 | Matyjaszewski et al. |
| 6,790,919 | B2 | 9/2004 | Matyjaszewski et al. |
| 6,887,962 | B2 | 5/2005 | Matyjaszewski et al. |
| 7,019,082 | B2 | 3/2006 | Matyjaszewski et al. |
| 7,049,373 | B2 | 5/2006 | Matyjaszewski et al. |
| 7,064,166 | B2 | 6/2006 | Matyjaszewski et al. |
| 7,125,938 | B2 | 10/2006 | Matyjaszewski et al. |
| 7,157,530 | B2 | 1/2007 | Matyjaszewski et al. |
| 7,332,550 | B2 | 2/2008 | Matyjaszewski et al. |
| 7,825,199 | B1 | 11/2010 | Matyjaszewski et al. |
| 8,273,823 | B2 | 9/2012 | Matyjaszewski et al. |
| 2004/0110753 | A1 | 6/2004 | Jackson et al. |
| 2004/0158076 | A1 | 8/2004 | Jackson et al. |
| 2005/0283021 | A1 | 12/2005 | Hamada et al. |
| 2007/0123646 | A1 | 5/2007 | Lele et al. |

FOREIGN PATENT DOCUMENTS

| | | |
|---|---|---|
| WO | 2005087819 A1 | 9/2005 |
| WO | 2007025086 A2 | 3/2007 |
| WO | 2007075817 A1 | 7/2007 |
| WO | 2008148000 A1 | 12/2008 |
| WO | 2012034043 A1 | 3/2012 |
| WO | 2012054700 A1 | 4/2012 |

OTHER PUBLICATIONS

Gao W., Liu W., Mackay J. A., Zalutsky M. R., Toone E. J. Chilkoti A., In situ growth of a stoichiometric PEG-like conjugate at a protein's N-terminus with significantly improved pharmacokinetics, PNAS, Sep. 8, 2009, vol. 106, No. 36, 15231-15236.

Hong J., Gong P., Xu D., Dong L., Yao S., Stabilization of chymotrypsin by covalent immobilization on amine-functionalized superparamagnetic nanogel, Journal of Biotechnology 128 (2007) 597-605.

Harris, J. M., Chess R. B., Effect of Pegylation on Pharmaceuticals, www.nature.com/reviews/drugdisc, Mar. 2003, vol. 2.

Duncan R., The Dawning Era of Polymer Therapeutics, Nature Reviews, Drug Discovery, vol. 2, May 2003, 347.

Nicolas J., Mantovani G., Haddleton D., M. Living Radical Polymerization as a Tool for the Synthesis of Polymer-Protein/Peptide Bioconjugates, Macromol. Rapid Commun. 2007, 28, 1083-1111.

Liu J., Bulmus V., Herlambang D. L., Barner-Kowollik C., Stenzel M. H., Davis T. P., In Situ Formation of Protein-Polymer Conjugates through Reversible Addition Fragmentation Chain Transfer Polymerization, Angew. Chem. It., Ed. 2007, 46, 3099-3103.

Le Droumaguet B., Velonia K., In Situ ATRP-Mediated Hierarchical Formation of Giant Amphiphile Bionanoreactors, Angew. Chem. Int. Ed. 2008, 47, 6263-6266.

Borner, H. G., Kuhnle H., Hentschel J., Making "Smart Polymers" Smarter: Modern Concepts to Regulate Functions in Polymer Science, Highlight, J. Polym. Sci. Part A: Polym Chem.: vol. 48 (2010).

Conner, R. E., Tirrell D. A., Non-Canonical Amino Acids in Protein Polymer Design, 2007, Polymer Reviews, 47:1, 9-28.

Zeng, Q., Li T., Cash B., Li S., Xie F., Wang Q., Chemoselective derivatization of a bionanoparticle by click reaction and ATRP reaction, Chem. Commun., 2007, 1453-1455.

Canalle L. A., Lowik D. W. P. M., Hest, J. C. M., Polypeptide-polymer bioconjugates, Chem. Soc. Rev., 2010, 39, 329-353.

Lele B. S., Murata H., Matyjaszewski K., Russell A. J., Synthesis of Uniform Protein-Polymer Conjugates, Biomacromolecules 2005, 6, 3380-3387.

Yan M., Liu Z., Lu D., Liu Z., Fabrication of Single Carbonic Anhydrase Nanogel against Denaturation and Aggregation at High Temperature, Biomacromolucules 2007, 8, 560-565.

Ge J., Lu D., Wang J. Liu Z., Lipase Nanogel Catalyzed Transesterification in Anhydrous Dimetryl Sulfoxide, Biomacromolucles 2009, 10, 1612-1618.

Ito, Y., Fujii H., Imanishi Y., Modification of Lipase with Various Synthetic Polymers and Their Catalytic Activities in Organic Solvent, Biotechnol. Prog. 1994, 10, 398-402.

Matyjaszewski K., Zia J., Atom Transfer Radical Polymerization, Chem. Rev. 2001, 2921-2990.

Wang J. S., Matyjawzewski K., Controlled/"Living" Radical Polymerization. Atom Transfer Radical Polymerization in the Presence of Transition-Metal Complexes, J. Am. Chem. Soc. 1995, 117, 5614-5615.

Heredia K. L., Bontempo D., Ly T. Byers J. T., Halstenberg S., Maynard H. D., In Situ Preparation of Protein—"Smart" Polymer Conjugates with Retention of Bioactivity, J. Am. Chem. Soc. 2005, 127, 16955-16960.

Yan M., Ge J., Liu Z., Ouyang P., Encapsulation of Single Enzyme in Nanogel with Enhanced Biocatalytic Activity and Stability, J. Am. Chem. Soc. 2006, 128, 11008-11009.

Broyer R. M., Quaker G., M., Maynard H. D., Designed Amino Acid ATRP Initiators for the Synthesis of Biohybrid Materials, J. Am. Chem. Soc., 2008, 130, 1041-1047.

Ge J., Lu D., Wang J. Yan M. Lu Y., Liu Z., Molecular Fundamentals of Enzyme Nanogels, J. Phys. Chem. B 2008, 112, 14319-14324.

Averick S., Simakova A., Park S., Konkolewisz D., Magenau A. J. D., Mehl R. A., Matyjaszewski K., ATRP under Biologically Relevant Conditions: Grafting from a Protein, ACS Macro Lett., 2012, 1, 6-10.

Stokes, A. L., Miyake-Stoner S. J., Peeler J. C., Nguyen D. P., Hammer R. P., Mehl R. A., Enhancing the utility of unnatural amino acid synthetases by manipulating broad substrate specificity, Mol. BioSyst., 2009, 5, 1032-1038.

Qiu J., Charleux B., Matyjaszewski K., Controlled/living radical polymerization in aqueous media: homogeneous and heterogeneous systems, Prog. Polym. Sci. 26 (2001) 2083-2134.

Davis K. A., Matyjaszewski K., Statistical, Gradient, Block, and Graft Copolymers by Controlled/ Living Radical Polymerizations, Advances in Polymer Science, vol. 159 @ Springer-Verlag Berlin Heidelberg 2002.

Depp, V., Alikhani A., Grammer V., Lele B. S., Native protein-initiated ATRP: A viable and potentially superior alternative to PEGylation for stabilizing biologics, Acta Biomaterialia 5 (2009) 560-569.

Averick, S. E., Magenau, A. J. D., Simakova, A., Woodman, B. F., Seong A., Mehl R., Matyjeszewski K., Covalently incorporated protein-nanogels using AGET ATRP in an inverse miniemulsion, Polym. Chem., 2011, 2, 1476-1478.

Averick, S. E., Magenau, A. J. D., Simakova, A., Woodman, B. F., Seong A., Mehl R., Matyjeszewski K., Supplementary Material (ESI) for Polymer Chemistry: Covalently incorporated protein-nanogels using AGET ATRP in an inverse miniemulsion, Polym. Chem., 2011, 2, 1476-1478.

Lutz, J., Borner, H. G., Modern trends in polymer bioconjugates design, Prog. Polym. Sci. 33 (2008) 1-39.

Miyake-Stoner, S. J., Miller, A. M., Hammill, J. T., Peller, J. C., Hess, K. R., Mehl, R. A., Brewer, S. H., Probing Protein Folding Using Site-Specifically Encoded Unnatural Amino Acids as FRET Donors with Tryptophan, Biochemistry 2009, 48, 5953-5962.

Miyake-Stoner, S. J., Refakis, C. A., Hammill, J. R., Lusic, H., Hazen, J. L., Deiters A., Mehl, R. A., Generating Permissive Site-Specific Unnatural Aminoacyl-tRNA Synthetases, Biochemistry 2010, 49, 1667-1677.

(56) References Cited

OTHER PUBLICATIONS

Boyer, C., Bulmus V., Davis, T. P., Ladmiral V., Liu J., Perrier S., Bioapplications of RAFT Polymerization, Chem. Rev. 2009, 109, 5402-5436.

Matyjaszewski K., Tsarevsky N. V., Nanostraauctured functional materaisl prepared by atom transfer radical polymerization, Nature Chemistry, vol. 1, Jul. 2009.

Pedelacq J-D., Cabantous S., Tran T., Terwilliger T. C., Waldo G. S., Engineering and characterization of a superfolder green fluorescent protein, Nature Biotechnology, vol. 24, No. 1, Jan. 2006.

PCT Notification of Transmittal of the International Search Report and the Written Opinion of the International Searching Authority, or the Declaration, dated Jan. 26, 2012, 6 pages.

Toshimasa Hamamoto, Masahiko Sisido, Takashi Ohtsuki and Masumi Taki, Synthesis of cyclic peptide/protein using the NEXT-A reaction followed by cyclization, Chem. Commun., 2011, 47, pp. 9116-9118.

Toshimasa Hamamoto, Masahiko Sisido, Takashi Ohtsuki and Masumi Taki, Synthesis of cyclic peptide/protein using the NEXT-A reaction followed by cyclization, Electronic Supplementary Material for Chemical Communications, The Royal Society of Chemistry 2011, pp. 1-24.

\* cited by examiner

GENETICALLY ENCODED INITIATOR FOR POLYMER GROWTH FROM PROTEINS

CROSS-REFERENCE TO RELATED APPLICATIONS

This application is a continuation of PCT International Application No. PCT/US2011/051043, filed Sep. 9, 2011, which claims priority under 35 U.S.C. §119 to U.S. Provisional Application No. 61/381,757; filed Sep. 10, 2010.

FIELD OF THE INVENTION

This invention pertains to the bioconjugation of polymers with proteins at specific sites on the protein.

BACKGROUND

The wide functional diversity of proteins catalysis, regulation, transport, and structure has made them desirable bioresponsive molecules for integration into materials and medicine. Protein-polymer bioconjugates have already shown an impressive range of altered or improved properties (see Borner et al., J. Polym. Sci. Part a-Polym. Chem. 2010, 48, 1; Depp et al., Acta Biomat. 2009, 5, 560; Gao et al., Proc. Nat. Acad. Sci. USA 2009, 106, 15231; Krishna et al., Biopolymers 2010, 94, 32; Lutz et al., Prog. Polym. Sci. 2008, 33, 1; Nicolas et al., Macromol. Rapid Comm. 2007, 28, 1083; Connor et al., Polym. Rev. 2007, 47, 9). Protein-polymer bioconjugates also have shown efficient pharmacokinetics and therapeutic potency (see Gao et al.; Krishna et al.; Lutz et al.; Nicolas et al.; Lele et al., Biomacromolecules 2005, 6, 3380).

Protein polymers bioconjugates have been prepared in two general ways: either by graft-to methods where a preformed functionalized polymer is attached to an amino acid, cofactor or end group, or by the graft-from method where a location on the purified protein is functionalized with an initiator and then the polymer is grown from that site (see Krishna et al.; Liu et al., Ang. Chem., Int. Ed. 2007, 46, 3099; Zeng et al., Chem. Comm. 2007, 1453; Heredia et al., J. Am. Chem. Soc. 2005, 127, 16955. Thus far, the graft-from methods employed for residue-specific incorporation of polymerization initiators into proteins are limited to the N-terminal position or specific natural amino-acid directed linkages (see Depp et al.; Gao et al.; Le Droumaguet et al., Ang. Chem., Int. Ed. 2008, 47, 6263; Lele et al.; Canalle et al., Chem. Soc. Rev. 2010, 39, 329. Both methods suffer from challenging purification of intermediates and/or the inability to efficiently control the number or location of polymer connections to the protein, which compromises protein structural integrity. While the many graft-to and graft-from experiments using natural amino acids on proteins have illustrated the immense potential impact of well-defined protein-polymer conjugates, their application is limited by technical shortcomings associated with their synthesis and purification.

Previous protein-polymers have been prepared using an atom transfer radical polymerization (ATRP) technique (see Wang et al., Am. Chem. Soc. 1995, 117, 5614; Matyjaszewski & Xia, Chem. Rev. 2001, 101, 2921; Matyjaszewski & Tsarevsky, Nature Chem. 2009, 1, 276) wherein an ATRP initiator attached to the protein provides a linkage between the protein and growing polymer chain.

Atom-transfer radical polymerization (ATRP) and other controlled/living radical polymerization (CRP) methodologies including nitroxide mediated polymerization (NMP) and reversible addition fragmentation transfer (RAFT) systems allow unprecedented control over polymer dimensions (molecular weight), uniformity (polydispersity), topology (geometry), composition and functionality. [Matyjaszewski, K., Ed. Controlled Radical Polymerization; ACS: Washington, D.C., 1998; ACS Symposium Series 685. Matyjaszewski, K., Ed.; Controlled/Living Radical Polymerization. Progress in ATRP, NMP, and RAFT; ACS: Washington, D.C., 2000; ACS Symposium Series 768; Matyjaszewski, K., Davis, T. P., Eds. Handbook of Radical Polymerization; Wiley: Hoboken, 2002; Qiu, J.; Charleux, B.; Matyjaszewski, K. Prog. Polym. Sci. 2001, 26, 2083; Davis, K. A.; Matyjaszewski, K. Adv. Polym. Sci. 2002, 159, 1.] ATRP is a controlled radical polymerization (CRP) technique; therefore, monomers and cross-linkers may be incorporated in a predictable, controlled, and programmed manner to yield polymer chains of essentially equal length, as defined by the ratio of consumed monomer to the added initiator. Moreover, the functionality present on the introduced initiator is preserved and forms both the α- and ω-chain end functionality on the formed polymer segment. The polymers synthesized using ATRP show tolerance to many functional groups, such as hydroxy, amino, amido, esters, carboxylic acid, that can be incorporated into a copolymer then used for post-polymerization modifications including covalent linking of biomolecules and drug delivery. As disclosed below, this enables formation of bioconjugates between synthetic polymers and biomolecules. Thus, the delivery system synthesized using ATRP offer customizable and tunable structure for precise targeted delivery of biologically active molecules.

Methods for the incorporation of an unnatural amino acid by use of an orthogonal synthetase-tRNA pair wherein the gene for the synthetase is randomized for the codons corresponding to the desired active-site residues is discussed by Xie & Schultz. Alternating positive and negative selection on the resulting library of synthetases produces clones which are transformed into cells with a plasmid containing a gene interrupted with an amber codon (see Miyake-Stoner & Refakis et al., Biochemistry 2010, 49, 1667; Stokes et al., Molecular Biosystems 2009, 5, 1032).

Techniques for the characterization of the incorporation of an initiator into proteins in response to the amber codon are described by Miyake-Stoner & Refakis et al.; Stokes et al.; Miyake-Stoner & Miller et al., Biochemistry 2009, 48, 5953.

Despite the importance of protein-polymer bioconjugates, there is no general method for producing homogeneous recombinant proteins that contain polymer initiators at defined sites (see Broyer et al., J. Am. Chem. Soc. 2008, 130, 1041).

INDUSTRIAL APPLICABILITY

This invention provides a general method for the quantitative, site-specific incorporation of a polymer initiator initially exemplified by an unnatural amino acid of formula 6, and further exemplified by the modified amino acid of formula 1, into a recombinant protein. This method overcomes the technical challenges of attaching an initiator to the protein of interest prior to polymerization and provides facile access to a diversity of sites on proteins. The utility of the initiators of formula 6 are exemplified by growing of oligo(ethylene oxide)monomethyl ether methacrylate polymers from a green fluorescent protein with initiator of formula 1 site-specifically incorporated on its surface and showing that the attached polymer does not affect the general structure or solubility of the green fluorescent protein. The resulting amide linkage between the protein and polymer should be sufficiently stable to allow use of the formed bioconjugate in drug delivery and material science applications. While we have shown that this initiator present on a specific non-interfering site on GFP functions well for generating protein-polymers in aqueous conditions by standard ATRP chemistry it should also function with other controlled radical polymerization agents as well. Procedures for transforming this specific functional group to functionality allowing other controlled radical polymerization procedures are well known in the art.

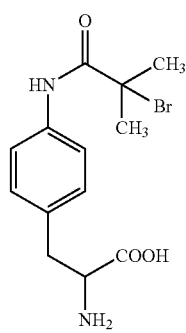

1

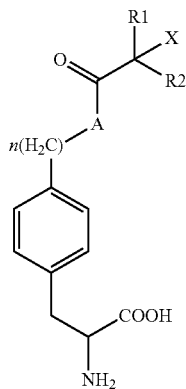

6

SUMMARY

An embodiment of this invention is a general method for the quantitative, site-specific incorporation into a recombinant protein of an unnatural amino acid further comprising a functionality that directly acts as a polymer initiator function as exemplified by the initiator of formula 6. The unnatural amino acid may alternatively comprise a functionality that can be converted into the desired initiating functionality. This method overcomes the technical challenges of directly attaching an initiator to a protein of interest prior to polymerization and provides facile access to a diversity of sites on proteins. The utility of this approach to forming functional proteins further comprising initiators for CRP is exemplified by the unnatural amino acid of formula 6. The utility of this approach is further exemplified by growing polymers of oligo(ethylene oxide)monomethyl ether methacrylate from a green fluorescent protein with initiator 1 site-specifically incorporated on its surface and showing that the attached polymer does not affect the general structure or solubility of the green fluorescent protein. The resulting amide linkage between the protein and polymer should be stable to drug delivery and material science applications. While we have shown that this initiator on GFP functions well for generating protein-polymers in aqueous conditions by standard ATRP chemistry it should also function with other controlled radical polymerization agents as well.

An embodiment of the invention is the unnatural amino acid of formula 6 and salts thereof, designed to be incorporated in a protein site-specifically and function as an initiator for atom-transfer radical polymerization.

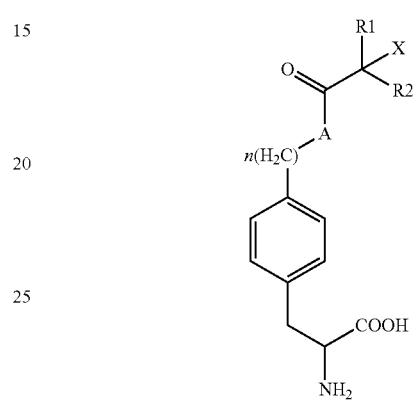

6

In the structure of unnatural amino acids of formula 6, R1 and R2 are independently H, C1-C8 alkyl, cycloalkyl, heterocycloalkyl, aryl, or heteroaryl; X is F, Cl, Br, I, $N_3$, alkoxyamine, or a thiocarbonyl thio moiety; A is O, S, or NR wherein R is H, C1-C8 alkyl, cycloalkyl, heterocycloalkyl, aryl, or heteroaryl; and n is 0, 1, 2, or 3.

A embodiment of the invention is an unnatural amino acid having the structure of formula 6 and salts thereof, wherein R1 and R2 are independently H, methyl, or phenyl; X is F, Cl, Br, or I; A is O, S, or NR, wherein R is H, methyl, or phenyl; and n is 1. Another embodiment of the invention is an unnatural amino acid is comprised of compounds wherein R1 and R2 are independently H, methyl, or phenyl; X is F, Cl, Br, or I; A is O; and n is 1 and are represented by the generic structure 7 and salts thereof.

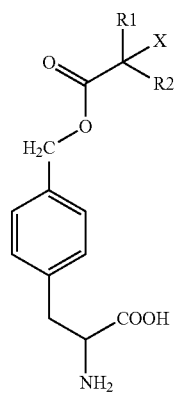

7

In another embodiment, the unnatural amino acid 7 has the structure 7b and salts thereof.

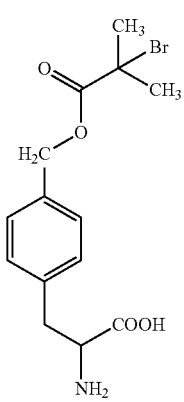
7b

An embodiment of the invention is the unnatural amino acid of formula 6 and salts thereof, wherein R1 and R2 are independently H, methyl, or phenyl; X is F, Cl, Br, or I; A is O, S, or NR, wherein R is H, methyl, or phenyl; and n is 0.

Another embodiment is an unnatural amino acid comprising the compounds of formula 6 wherein R1 and R2 are independently H, methyl, or phenyl; X is F, Cl, Br, or I; A is O; and n is 0 and is represented by the generic structure of formula 8 and salts thereof.

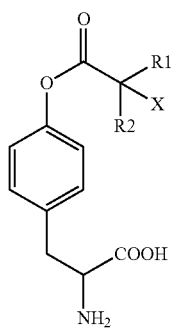
8

In yet another embodiment, the unnatural amino acid has the structure of formula 8b and salts thereof

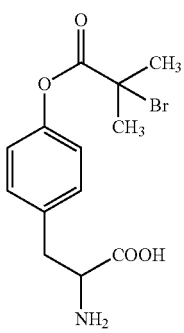
8b

Another embodiment of the invention is the unnatural amino acid of formula 6 and salts thereof, wherein R1 and R2 are independently H, methyl, or phenyl; X is F, Cl, Br, or I; A is NR, wherein R is H, methyl, or phenyl; and n is 0, and is represented by the generic structure of formula 9 and salts thereof

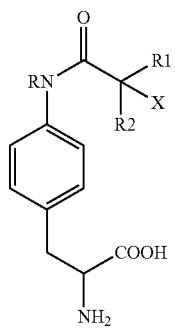
9

In another embodiment, the unnatural amino acid has the structure of formula 1 and salts thereof.

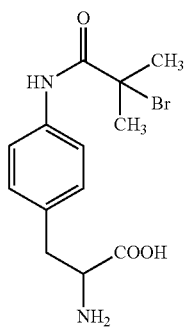
1

Another embodiment of the invention is a method of preparing the unnatural amino acid of formula 6, said method comprising the steps of
(a) providing an N-Boc-protected tyrosine derivative of formula 4,

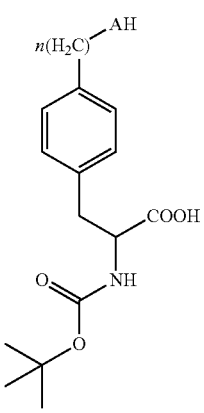
4

(b) reacting said derivative of formula 4 with an acyl halide of formula 10,

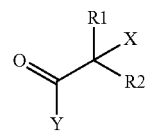
10 optionally in the presence of a base, to produce an N-Boc-protected intermediate of formula 5,

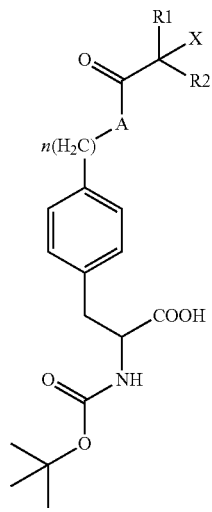

(c) deprotecting said intermediate of formula 5 to form salt compound of formula 6a,

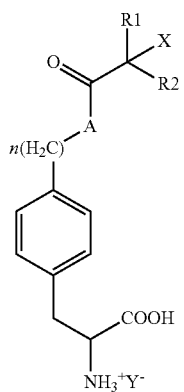

and (d) neutralizing said salt compound with base to produce said unnatural amino acid of formula 6.

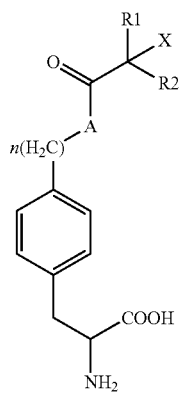

wherein R1 and R2 are independently H, C1-C8 alkyl, cycloalkyl, heterocycloalkyl, aryl, or heteroaryl; X is F, Cl, Br, I, N$_3$, alkoxyamine, or a thiocarbonyl thio moiety; A is O, S, or NR, wherein R is H, C1-C8 alkyl, cycloalkyl, heterocycloalkyl, aryl, or heteroaryl; and n is 0, 1, 2, or 3. In another embodiment of the process, R1 and R2 are independently H, methyl, or phenyl; X is F, Cl, Br, or I; Y is F, Cl, Br, I, or trifluoroacetate; A is O, S, or NR, wherein R is H, methyl, or phenyl; and n is 1. In another embodiment of the inventive process, R1 and R2 are H, methyl, or phenyl; X is Br; Y is Cl or Br; A is O or NH.

It is an embodiment of the inventive method disclosed above to prepare compounds of formula 6 wherein R1 and R2 are independently H, methyl, or phenyl; X is F, Cl, Br, or I; Y is F, Cl, Br, I, or trifluoroacetate; A is O, S, or NR, wherein R is H, methyl, or phenyl; and n is 0. In another embodiment of the inventive method disclosed above to prepare compounds of formula 6, R1 and R2 are H, methyl, or phenyl; X is Br; Y is Cl or Br; A is O or NH; and n is 0, are prepared.

It is an embodiment of the invention to deprotect the intermediate of formula 5 by treatment with hydrogen chloride in dioxane, trifluoroacetic acid, or other suitable deprotection medium to afford compounds of formula 6a.

An embodiment of the invention is a protein-based initiator comprising an unnatural amino acid or its salt thereof, wherein said unnatural amino acid comprises an initiator for a controlled polymerization process and wherein the unnatural amino acid is incorporated site-specifically within the protein via translation using an orthogonal aminoacyl-tRNA synthetase/orthogonal tRNA pair and selector codon. In one embodiment of the invention, the protein-based initiator comprises an unnatural amino acid of formula 6 or a salt thereof, wherein R1 and R2 of said amino acid initiator are independently H, C1-C8 alkyl, cycloalkyl, heterocycloalkyl, aryl, or heteroaryl; X is F, Cl, Br, I, N$_3$, alkoxyamine, or a thiocarbonyl thio moiety; A is O, S, or NR, wherein R is H, C1-C8 alkyl, cycloalkyl, heterocycloalkyl, aryl, or heteroaryl; and n is 0, 1, 2, or 3.

Another embodiment of the invention is a method of preparing a protein-based initiator containing a site-specifically incorporated unnatural amino acid of formula 6 comprising an initiator functionality, where the method comprises the steps, (a) providing a nucleic acid, wherein the nucleic acid further includes a selector codon; and (b) providing a translation system, wherein the nucleic acid is translated by the translation system to encode a protein, and wherein the translation system further comprises, (i) an orthogonal tRNA that recognizes the selector codon;

(ii) an unnatural amino acid initiator of formula 6 or salt thereof; and (iii) an orthogonal aminoacyl-tRNA synthetase that preferentially aminoacylates the orthogonal tRNA with the initiator amino acid 6 to produce the initiator protein having 6 incorporated at specific sites on the protein, wherein said amino acid initiator of formula 6, R1 and R2 are independently H, C1-C8 alkyl, cycloalkyl, heterocycloalkyl, aryl, or heteroaryl; X is F, Cl, Br, I, N$_3$, alkoxyamine, or a thiocarbonyl thio moiety; A is O, S, or NR, wherein R is H, C1-C8 alkyl, cycloalkyl, heterocycloalkyl, aryl, or heteroaryl; and n is 0, 1, 2, or 3. In one embodiment, the method uses an unnatural amino acid initiator of formula 7. In another embodiment, the method uses and unnatural amino acid initiator of formula 8. In yet another embodiment, the method uses an unnatural amino acid initiator of formula 9. In another embodiment, the method uses an unnatural amino acid initiator of formula 1.

An embodiment of the invention is a method of preparing a site-specific protein-polymer bioconjugate from a protein-based initiator incorporating an unnatural amino acid herein exemplified by an initiator of formula 6 or salt thereof, comprising the step of, (a) reacting said protein-based initiator with monomers under standard atom transfer radical polymerization techniques to produce said protein-polymer bioconjugates, whereby the polymer attachments are at specifically selected sites on the protein wherein said amino acid initiator of formula 6, R1 and R2 are independently H, C1-C8 alkyl, cycloalkyl, heterocycloalkyl, aryl, or heteroaryl; X is F, Cl, Br, I, $N_3$, alkoxyamine, or a thiocarbonyl thio moiety; A is O, S, or NR, wherein R is H, C1-C8 alkyl, cycloalkyl, heterocycloalkyl, aryl, or heteroaryl; and n is 0, 1, 2, or 3.

In another embodiment, the above method for preparing a site-specific protein-polymer bioconjugate the protein-based initiator incorporates an initiator amino acid of formula 7. In a different embodiment, the protein-based initiator incorporates an unnatural initiator amino acid of formula 8. In another embodiment, the protein-based initiator incorporates an unnatural initiator amino acid of formula 9. In an additional embodiment, the protein-based initiator incorporates an unnatural initiator amino acid of formula 1.

DEFINITIONS

The term "selector codon" refers to a codon recognized by the O-tRNA in the translation process and not typically recognized by an endogenous tRNA. The O-tRNA anticodon loop recognizes the selector codon on the mRNA and incorporates its amino acid, e.g., an initiator amino acid, at this site in the polypeptide. Selector codons can include, e.g., nonsense codons, such as stop codons (e.g., amber, ochre, and opal codons), four or more base codons, rare codons, codons derived from natural or unnatural base pairs, or the like.

The term "translation system" refers to the components that incorporate an amino acid into a growing polypeptide chain (protein). Components of a translation system can include, e.g., ribosomes, tRNAs, synthetases, mRNA, and the like. Typical translation systems include cells, such as bacterial cells (e.g., *Escherichia coli*), archeaebacterial cells, eukaryotic cells (e.g., yeast cells, mammalian cells, plant cells, insect cells), or the like. Alternatively, the translation system comprises an in vitro translation system, e.g., a translation extract including a cellular extract. The O-tRNA or the O-RSs of the invention can be added to or be part of an in vitro or in vivo translation system, e.g., in an eukaryotic cell, e.g., a bacterium (such as *E. coli*), or in a eukaryotic cell, e.g., a yeast cell, a mammalian cell, a plant cell, an algae cell, a fungus cell, an insect cell, or the like. The translation system can also be a cell-free system, e.g., any of a variety of commercially available in vitro transcription/translation systems in combination with an O-tRNA/O-RS pair and an initiator amino acid as described herein.

The translation system may optionally include multiple O-tRNA/O-RS pairs, which allow incorporation of more than one unnatural amino acid, e.g., an initiator amino acid and another unnatural amino acid. For example, the cell can further include an additional different O-tRNA/O-RS pair and a second unnatural amino acid, where this additional O-tRNA recognizes a second selector codon and this additional O-RS preferentially aminoacylates the O-tRNA with the second unnatural amino acid. For example, a cell that includes an O-tRNA/O-RS pair (where the O-tRNA recognizes, e.g., an amber selector codon) can further comprise a second orthogonal pair, where the second O-tRNA recognizes a different selector codon (e.g., an opal codon, four-base codon, or the like). Desirably, the different orthogonal pairs are derived from different sources, which can facilitate recognition of different selector codons.

Matyjaszewski and coworkers disclosed the fundamental four component Atom Transfer Radical Polymerization (ATRP) process comprising the addition, or in situ formation, of an initiator, in this case a molecule with a transferable atom or group that is completely incorporated into the final product, a transition metal and a ligand that form, a partially soluble transition metal complex that participates in a reversible redox reaction with the added initiator or a dormant polymer to form the active species to copolymerize radically polymerizable monomers, and a number of improvements to the basic ATRP process, in a number of patents and patent applications: U.S. Pat. Nos. 5,763,546; 5,807,937; 5,789,487; 5,945,491; 6,111,022; 6,121,371; 6,124,411; 6,162,882; 6,624,262; 6,407,187; 6,512,060; 6,538,091; 6,541,580; 6,624,262; 6,627,314; 6,759,491; 6,790,919; 6,887,962; 7,019,082; 7,049,373; 7,064,166; 7,125,938; 7,157,530; 7,332,550 and U.S. patent application Ser. No. 09/534,827; PCT/US04/09905; PCT/US05/007264; PCT/US05/007265; PCT/US06/33152; PCT/US2006/048656 and PCT/US08/64710, all of which are herein incorporated by reference to provide both background and definitions for the terms used herein. Papers include Wang et al., *Am. Chem. Soc.* 1995, 117, 5614; Matyjaszewski & Xia, *Chem. Rev.* 2001, 101, 2921; Matyjaszewski & Tsarevsky, *Nature Chem.* 2009, 1, 276.

An "amino acid initiator" is, in this case a molecule containing a primary amine functionality and carboxylic acid functionality that can be incorporated into a protein primary sequence with a transferable atom or group that is completely incorporated into the final product, a transition metal and a ligand that form, a partially soluble transition metal complex that participates in a reversible redox reaction with the added initiator or a dormant polymer to form the active species to copolymerize radically polymerizable monomers.

A "protein-based initiator" is where an amino acid initiator has been incorporated into the primary sequence of a protein producing a protein with a transferable atom or group that is completely incorporated into the final product, a transition metal and a ligand that form, a partially soluble transition metal complex that participates in a reversible redox reaction with the added initiator or a dormant polymer to form the active species to copolymerize radically polymerizable monomers.

BRIEF DESCRIPTION OF THE DRAWINGS

FIG. 4a is an ESI-MS-T of analysis of sfGFP showing a single major peak at 27827.0 Da±1 Da. FIG. 4b is an ESI-MS-T of analysis of GFP-1 showing a single major peak at 28024.0 Da±1 Da. These spectra show the expected molecular weigh difference of 197 Da from native indicating a single efficient incorporation of 1 at the expected site. Each sample did show a small peak at −131±1 Da indicating minor amounts of peptidase-based removal of N-terminal methionines and +22 sodium adducts. No other peaks were observed that would correlate with background incorporation of a natural amino acid.

FIG. 5a is the experimentally observed isotopic pattern for $[M+2H]^{2+}$ at 589-592 Da. FIG. 5b is the predicted isotopic pattern for $[C_{50}H_{77}N_{14}O_{14}Br+2H]^{2+}$ as derived from various on-line isotopic pattern generators.

DETAILED DESCRIPTION OF THE EMBODIMENT(S)

Figure 1:
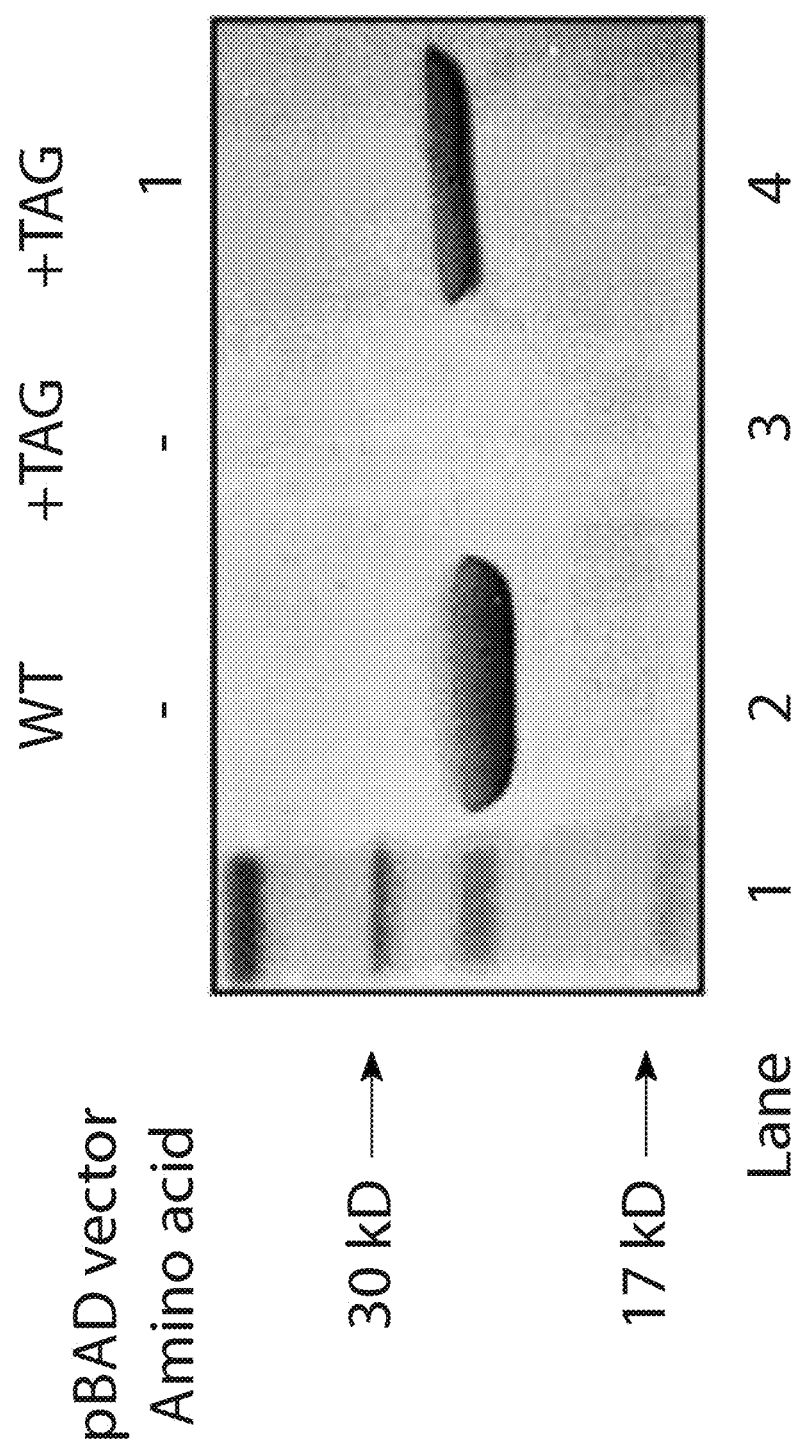
FIG. 1 shows the genetic incorporation of ATRP initiator into proteins. The evolved MjRS/tRNA$_{CUA}$ pair in pDule-BIBAF allows for site-specific incorporation of 1 in response to an amber codon. Lane 2 shows expression levels of GFP-wt from pBad-GFP-His$_6$. Production of GFP-1 from pBad-GFP-134TAG-His$_6$ is dependent on 1 in the growth media, lane 3 without 1 present, lane 4 with 1 mM 1 present. Protein was purified by Co$^{+2}$ affinity chromatography, separated by SDS-PAGE and stained with Coomassie.

The inventors have discovered that site-specific incorporation of polymers onto proteins can be achieved via the novel techniques described herein. An exemplary novel unnatural amino acid, 4-(2'-bromoisobutyramido)phenylalanine 1 (See FIG. 9) was designed as an exemplary amino acid to demonstrate the principle disclosed herein. This amino acid was synthesized and incorporated into a specific site in a protein where it would function as an initiator in an atom-transfer radical polymerization ("ATRP") after incorporation into the protein. A *Methanococcus jannaschii* tyrosyl-tRNA synthetase/tRNA$_{CUA}$ ("MjTyrRS/tRNA$_{CUA}$") pair was evolved to genetically encode amino acid 1 in response to an amber codon. To demonstrate the utility of this initiator we produced Green Fluorescent Protein ("GFP") with the functionalized unnatural amino acid 1 site-specifically incorporated on its surface ("GFP-1"). Purified GFP-1 was then used as an initiator under standard ATRP conditions with the monomer, oligo(ethylene oxide)monomethyl ether methacrylate ("MPEG"), efficiently producing a polyMPEG-GFP bioconjugate where the polymer is connected at the selected site on GFP.

The unnatural amino acid containing an ATRP initiator functionality, 1, was prepared as outlined in Scheme 1. Initiator 1 may be used directly in the subsequent reactions or its hydrochloride salt 1a may be used and neutralized under the reaction conditions to afford GFP-1. It is important to synthesize 1 in large quantities since relatively large quantities of initiator-containing protein are needed for polymerization experiments. The synthetic route need not be asymmetric since the M/RS only utilizes the L form. The initiator 1a was synthesized in two steps in 63% yield from commercially available material. The salt was neutralized with base, for example one equivalent of NaOH, to afford initiator 1.

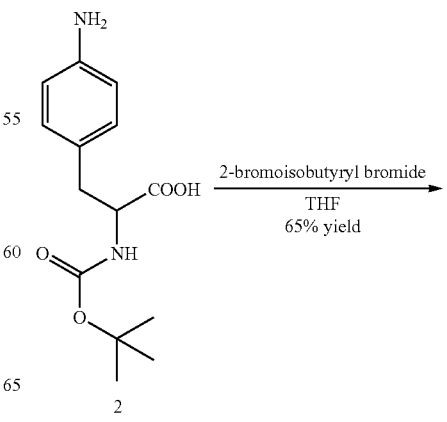

Scheme 1

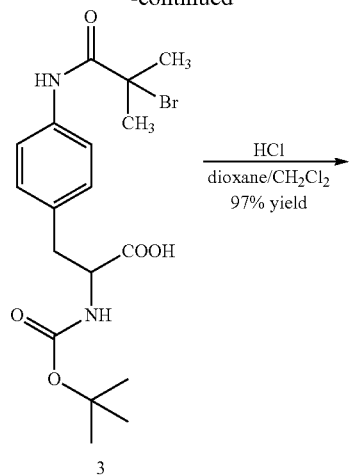

3

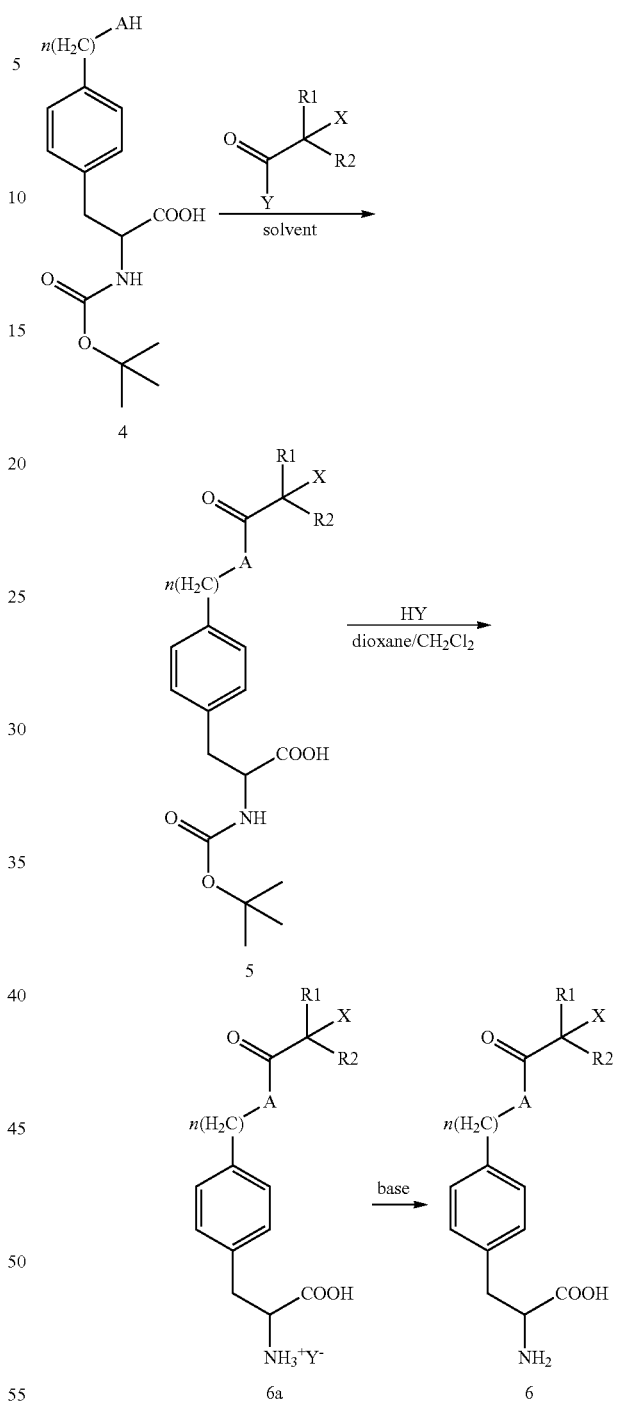

Scheme 2

Initiator 1 is an exemplification of a wider class of functional unnatural amino acids that the inventors have discovered are useful for the site-specific incorporation of the initiator functionality into proteins, thereby allowing site specific incorporation of grafting of polymers into proteins. In addition to acyl derivatives of 4-aminophenylalanine as initiators, acyl derivatives of tyrosine and other initiators having at least one methylene spacer between the amide or ester group and the benzene ring of the amino acid have been found to be useful for the invention. One class of these unnatural amino acids, with incorporated initiator functionality, is represented by the generalized structure 6. Initiator 6 may be prepared by the synthesis route shown in Scheme 2, wherein R1 and R2 are independently H, C1-C8 alkyl, cycloalkyl, heterocycloalkyl, aryl, or heteroaryl; X is F, Cl, Br, or I; Y is F, Cl, Br, I, or trifluoroacetate; A is O, S, or NR, wherein R is H, C1-C8 alkyl, cycloalkyl, heterocycloalkyl, aryl, or heteroaryl; and n is 0, 1, 2, or 3. While this definition of substituents provides an unnatural amino acid with an initiating group suitable for ATRP the utility of this exemplary unnatural amino acid can be modified to provide functionality for other CRP procedures. For example, X may also comprise an alkoxyamine for nitroxide mediated polymerization or a thiocarbonyl thio moiety suitable for a reversible addition fragmentation transfer polymerization.

The N-boc protected intermediate 4 can be purchased commercially or readily prepared by methods well known in the art.

Intermediate 4 is reacted with an α-haloacylhalide optionally in the presence of a base to afford protected compound 5. Reactions may be done at ambient temperature in a non-protic solvent. Suitable solvents include the ether solvents as tetrahydrofuran, ether, dioxane, and glyme, aromatic solvents as benzene and toluene, halogenated solvents such as methylene chloride, chloroform, carbontetrachloride, and chlorobutane. Generally, no additional bases are needed when A is nitrogen. When A is oxygen or sulfur it is useful to have a tertiary amine base, such as N,N-diisopropylethylamine, present in the reaction mixture.

The N-boc protecting group may be removed by reacting 5 with an acid halide in dioxane/methylene chloride or other suitable deprotection agent, such as trifluoroacetic acid, to afford the salt 6a.

The initiator 6a is readily neutralized in the presence of base to afford initiator 6. Typically 6a can be neutralized by one equivalent of a base, such as one equivalent of sodium hydroxide to afford 6 immediately prior to use in subsequent initiator reactions. Alternatively, 6a may be used and neutralized under reaction conditions to afford the protein-based initiator comprising 6. Both initiators 6a and 6 may be used as reactants for evolving the orthogonal pair and incorporating the desired initiating functionality into specific sites within the protein of interest.

It is desirable to prepare synthesize 6a or 6 in large quantities since relatively large quantities of the protein-based initiator are needed for polymerization experiments. The synthetic route need not be asymmetric since the MjRS only utilizes the L form of the unnatural amino acid 6.

In an embodiment of the invention, the initiators include 7a and 7 having a methylene spacer between the amino acid phenyl group and the ester group. These compounds are analogous to compounds of general structures 6a and 6 wherein n is 1 and A is O, and wherein R1 and R2 are independently H, C1-C8 alkyl, cycloalkyl, heterocycloalkyl, aryl, or heteroaryl; X is F, Cl, Br, or I; Y is F, Cl, Br, I, or trifluoroacetate.

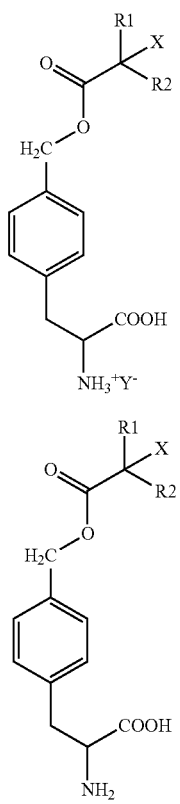

In another embodiment, initiators include the ester derivatives 8a and 8. These compounds are analogous to compounds of general structures 6a and 6 wherein n is 0 and A is O, and wherein R1 and R2 are independently H, C1-C8 alkyl, cycloalkyl, heterocycloalkyl, aryl, or heteroaryl; X is F, Cl, Br, or I; Y is F, Cl, Br, I, or trifluoroacetate.

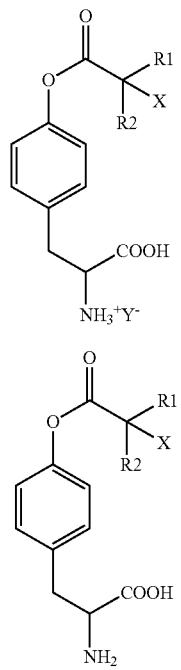

In another embodiment, the initiators include the amide derivatives 9a and 9. These compounds are analogous to compounds of general structures 6a and 6 wherein n is 1 and A is NR, wherein R is H, methyl, or phenyl; and wherein R1 and R2 are independently H, C1-C8 alkyl, cycloalkyl, heterocycloalkyl, aryl, or heteroaryl; X is F, Cl, Br, or I; Y is F, Cl, Br, I, or trifluoroacetate.

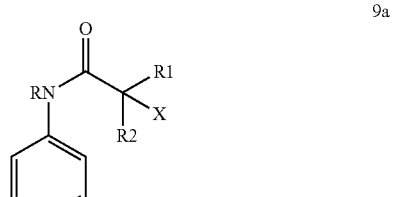

Table X is a partial listing of some of the unnatural initiator amino acids that may be prepared by the methods described above. Data for prepared compounds is given.

TABLE 1

Partial listing of exemplary unnatural amino acid initiators 6 and 6a.

| Comp. | R1 | R2 | X | Y | A | R | n | Physical Data |
|---|---|---|---|---|---|---|---|---|
| a (1) | Me | Me | Br | — | N | H | 0 | $^1$H NMR (500 MHz, D$_2$O): δ 7.6 (d, 2 H, Ar H), δ 7.2 (d, 2 H, Ar H). δ 4.1 (t, 1 H, CH), δ 3.4, 3.2 (dd, 2 H, CH$_2$), δ 2.0 (s, 6 H, CH$_3$). LCMS m/z for C$_{13}$H$_{17}$BrN$_2$O$_3$ [M + H]$^+$: 330.19; found: 329.3 and 331.2. |
| b | Me | Me | Cl | — | N | H | 0 | |
| c | Me | Me | I | — | N | H | 0 | |
| d | Me | Me | F | — | N | H | 0 | |
| e | H | Me | Br | — | N | Et | 0 | |
| f | H | i-Pr | Br | — | N | Me | 0 | |
| g | Me | c-Bu | Br | — | N | Me | 0 | |
| h | Me | 2- | Br | — | N | Me | 0 | |
| i | Ph | H | Br | Cl | N | Me | 0 | $^1$H NMR (500 MHz, DMSO): δ 9.9 (s, 3 H, NH$_3$), δ 7.5-7.0 (m, 9 H, Ar H), δ 5.6 (s, 1 H, CH), δ 4.6 (t, 1 H, C$_\alpha$—H), δ 3.1 (d, 2 H, CH$_2$). LCMS m/z for C$_{13}$H$_{17}$BrN$_2$O$_3$ [M + H]$^+$: 378.23; found: 377.2 and 379.2. |
| j (1a) | Me | Me | Br | Cl | N | H | 0 | $^1$H NMR (500 MHz, DMSO): δ 9.8 (s, 1 H, NH), δ 8.4 (s, 3 H, NH$_3$), δ 7.6 (d, 2 H, Ar H), δ 7.2 (d, 2 H, Ar H), δ 4.1 (bs, 1 H, CH), δ 3.1 (d, 2 H, CH$_2$), δ 2.0 (s, 6 H, CH$_3$). $^{13}$C NMR (500 MHz, DMSO): δ171.0 (1 C), δ170.0 (1 C), δ138.5 (1 C), δ130.9 (1 C), δ130.3 (2 C), δ121.2 (2 C), δ67.0 (dioxane), δ61.5(1 C), δ53.9(1 C), δ35.8(1 C), δ31.5.0 (2 C). FT-IR (CH$_3$CN) ν$_{max}$ cm$^{-1}$ 3374, 2977, 1740, 1664, 1600, 1522, 1416, 1112, 840, 529. LCMS m/z for C$_{13}$H$_{17}$BrN$_2$O$_3$ [M + H]$^+$: 330.19; found: 329.3 and 331.2. HRMS calculated 329.0501, found 329.0507 (i-Fit 0.7). |
| k | 2-Pyridyl | Me | Cl | I | N | H | 0 | |
| l | Me | Me | Br | TFA | N | H | 0 | |
| m | Me | H | Br | — | O | — | 0 | |
| n | Me | Me | Br | — | O | — | 0 | $^1$H-NMR (500 MHz, D$_2$O): δ 7.2 (dd, 4 H, Ar H), δ 5.1 (s, 2 H, Ar—CH$_2$—O), δ 4.1 (t, 1 H, C$_\alpha$—H), δ 3.2, 3.1 (dd, 2 H, CH$_2$), δ 1.9 (s, 6 H, C—(CH$_3$)$_2$Br). LCMS m/z for C$_{13}$H$_{17}$BrN$_2$O$_3$ [M + H]$^+$: 345.20; found: 344.1 and 346.1 |
| o | i-Bu | H | Cl | — | O | — | 0 | |
| p | H | Ph | Cl | — | O | — | 0 | |
| q | Me | Me | Br | Cl | O | — | 0 | $^1$H NMR (500 MHz, DMSO): δ 8.7 (s, 2 H, NH$_2$), δ 7.4 (d, 2 H, Ar H), 7.1 (d, 2 H, Ar H). δ 4.1 (bs, 1 H, CH), δ 3.4 (dd, 2 H, CH$_2$), δ 2.0 (s, 6 H, CH$_3$). LCMS m/z for C$_{13}$H$_{17}$BrN$_2$O$_3$ [M + H]$^+$: 331.17; found: 330.1 and 332.1. |
| r | H | Ph | Br | Cl | O | — | 0 | |
| s | Me | Me | Br | — | S | — | 0 | |
| t | Me | Me | Cl | — | S | — | 0 | |
| u | Me | Me | Br | Cl | S | — | 0 | |
| v | Me | Me | Br | — | N | H | 1 | |
| w | Me | H | Br | — | N | H | 1 | |
| x | Me | Me | Br | — | S | — | 1 | |
| y | Me | Me | Br | Cl | O | — | 1 | $^1$H-NMR (500 MHz, DMSO): δ 8.4 (s, 3 H, NH$_3$), δ 7.3 (dd, 4 H, Ar H), δ 5.2 (s, 2 H, Ar—CH$_2$—O), δ 4.2 (bs, 1 H, C$_\alpha$—H), δ 3.1 (d, 2 H, CH$_2$), δ 1.9 (s, 6 H, C—(CH$_3$)$_2$Br). LCMS m/z for C$_{13}$H$_{17}$BrN$_2$O$_3$ [M + H]$^+$: 345.20; found: 344.1 and 346.1. |
| z | Me | Me | Br | — | O | — | 2 | |

Figure 9:
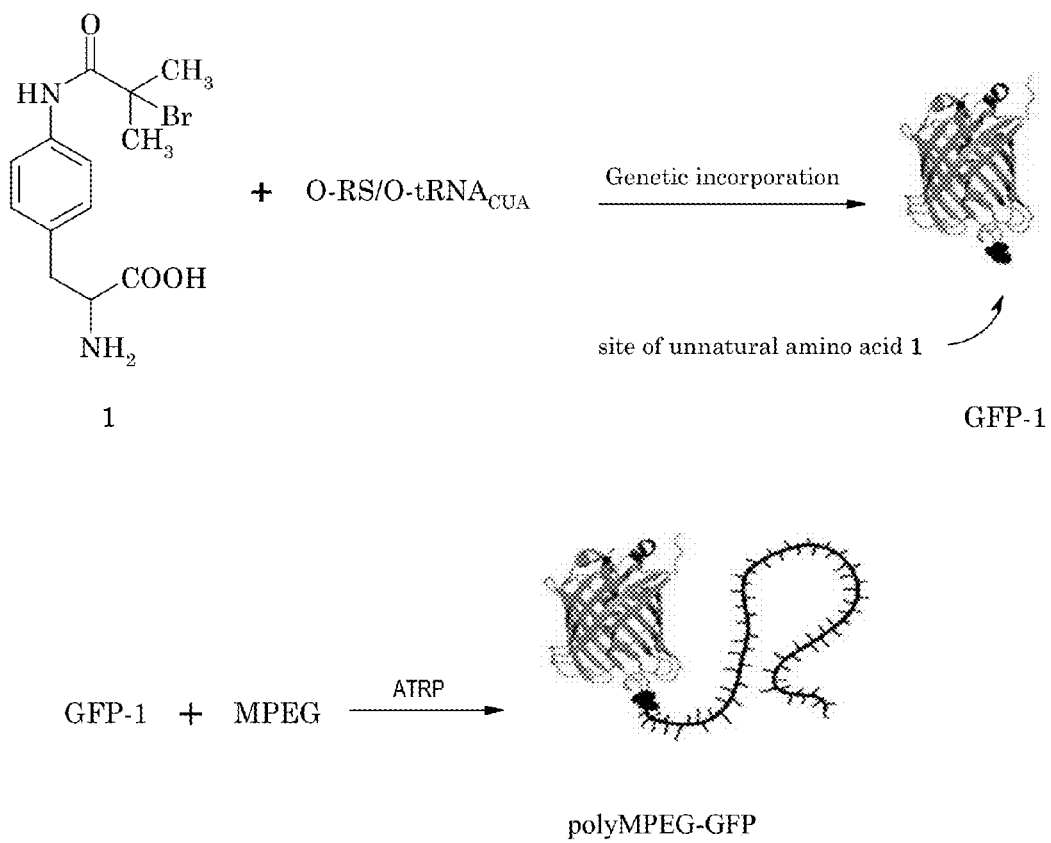
FIG. 9 is a reaction scheme illustrating the site specific incorporation of an unnatural amino acid initiator on a green fluorescent protein ("GFP") that is further used in an atom-transfer radical polymerization ("ATRP") reaction.

FIG. 9 is an exemplification of the overall method of preparing a recombinant protein-polymer. First, an orthogonal tRNA pair capable of incorporating 1 is evolved and a library of synthetase gene is randomized for codons specific to the desired site residue. Next, unnatural amino acid comprising an initiator functionality, 1, is site-specifically incorporated into the GFP to produce the protein-based initiator GFP-1. GFP-1 is then reacted with a monomer MPEG under ATRP reaction conditions to afford the recombinant protein-polymer, polyMPEG-GFP.

Figure 2:
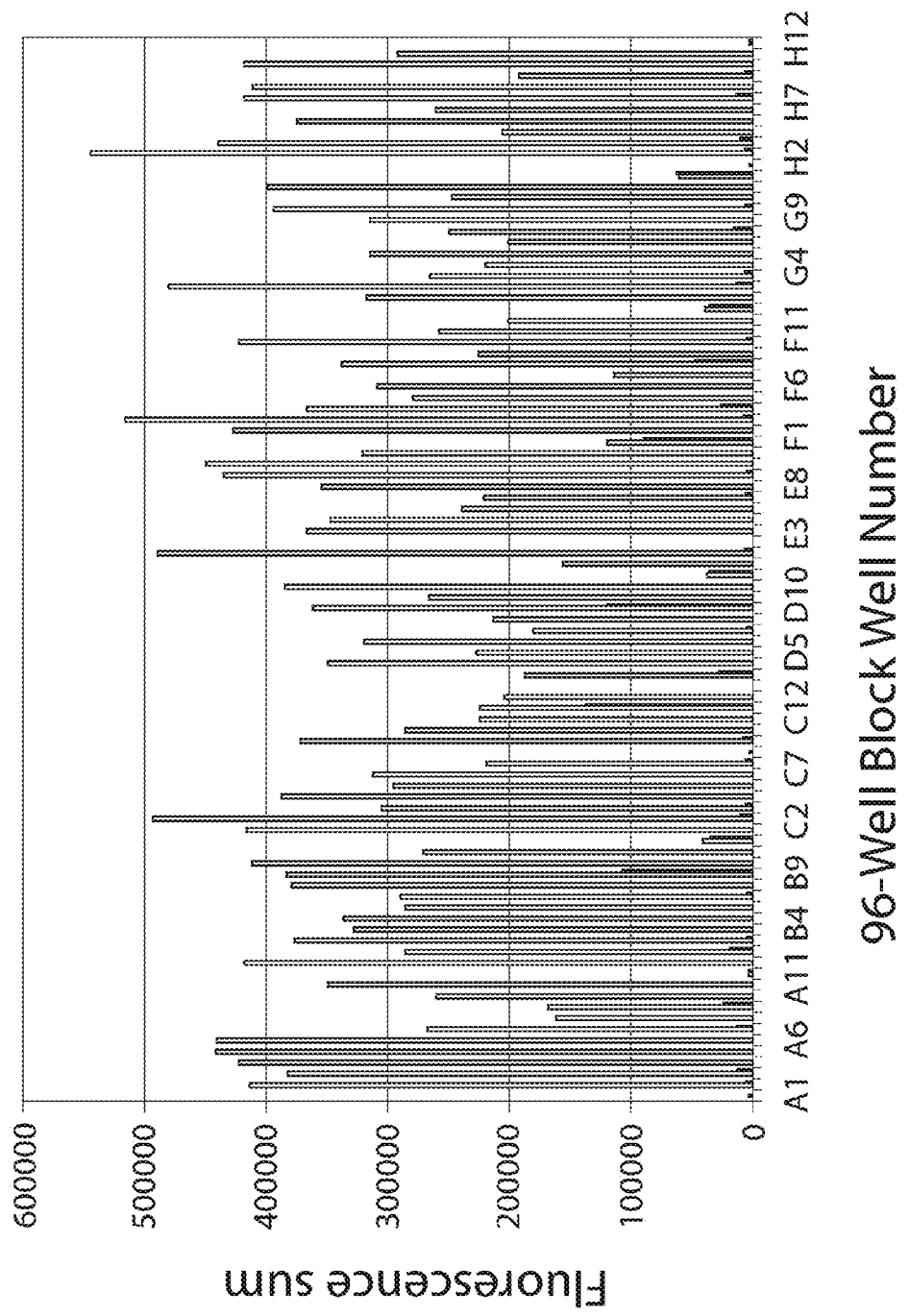
FIG. 2 shows the fluorescence measurements of 92 synthetases with GFP clones. The lighter lines represent colonies induced in media containing 1 mM 1 while darker black lines represent colonies induced in the absence of UAA.

In order to prepare protein-based initiator GFP-1 wherein 1 is site-specifically incorporated, we evolved an orthogonal MjTyrRS/tRNA$_{CUA}$ pair capable of incorporating exemplary nonlimiting unnatural amino acid 1 in response to an amber codon. We produced a library of the synthetase (RS) gene that was randomized for the codons corresponding to six active-site residues (Y32, L65, F108, Q109, D158, I159) within 7 Å of the bound tyrosine. Two rounds of alternating positive and negative selection were conducted on this library. The clones that survived the selection were transformed into cells with a plasmid containing a green fluorescent protein gene interrupted with an amber codon. A total of 92 colonies were assessed for UAA-dependent expression of GFP. The top eight performing clones showed greater than 400 mg/L of GFP-1 expression in the presence of 1 and no detectable GFP fluorescence over background in the absence of 1 (see FIG. 2). Sequencing these eight clones revealed five different RS sequences (see Table 2, Example 4).

Figure 4A:
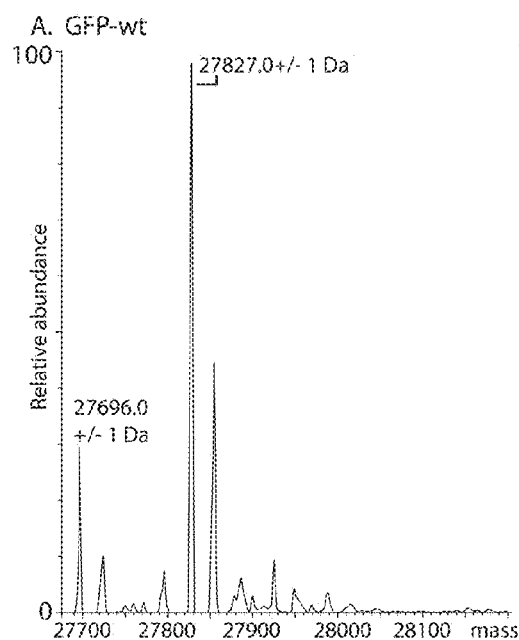
FIGS. 4a and 4b are the respective ESI-MS of GFP-wt and GFP-1 proteins and demonstrate the efficient high fidelity incorporation of a single 1 in response to an amber stop codon.
Figure 4B:
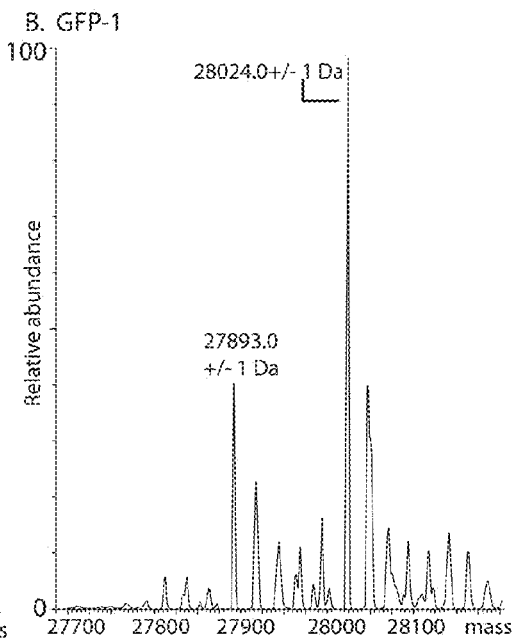
Figure 5A:
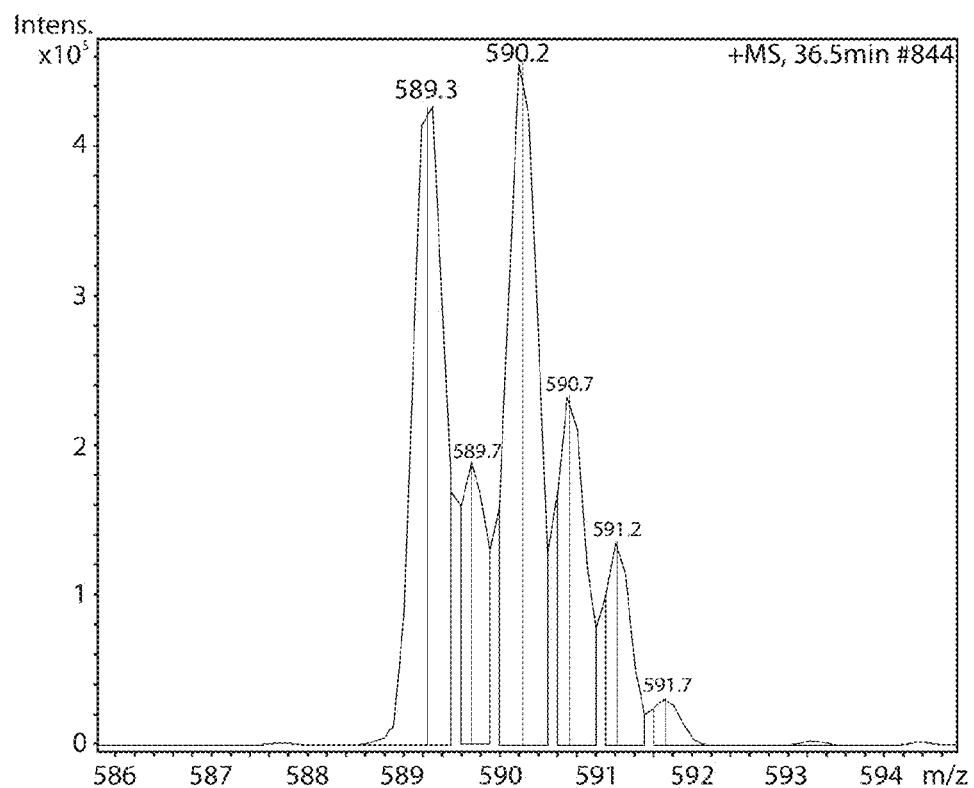
FIGS. 5a and 5b are isotopic abundance patterns indicating the presence of bromine.
Figure 5B:
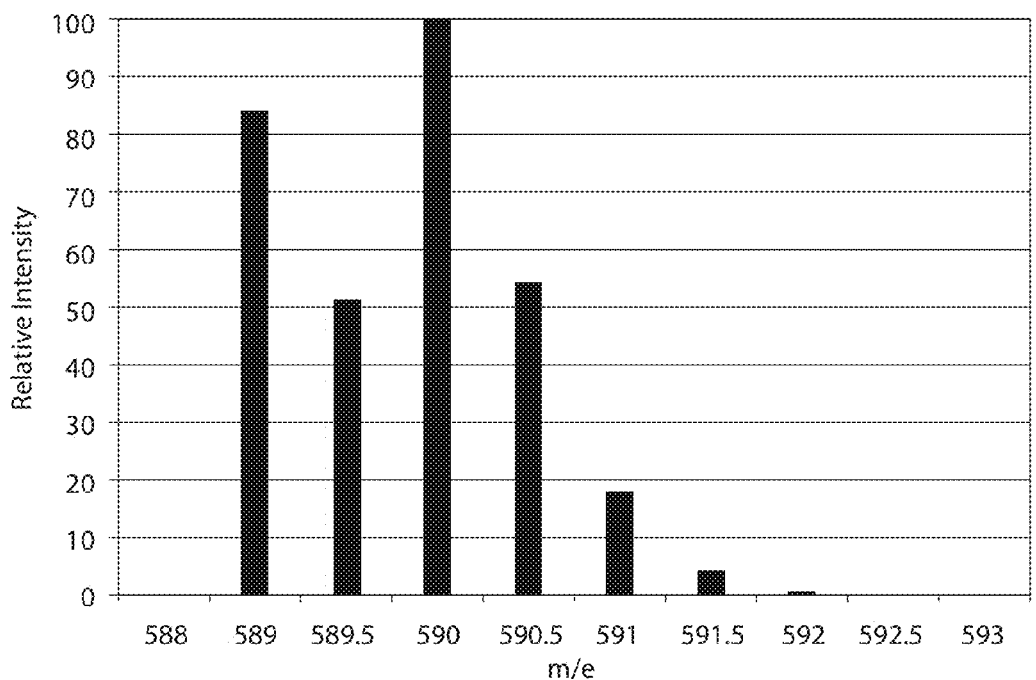
Figure 6:
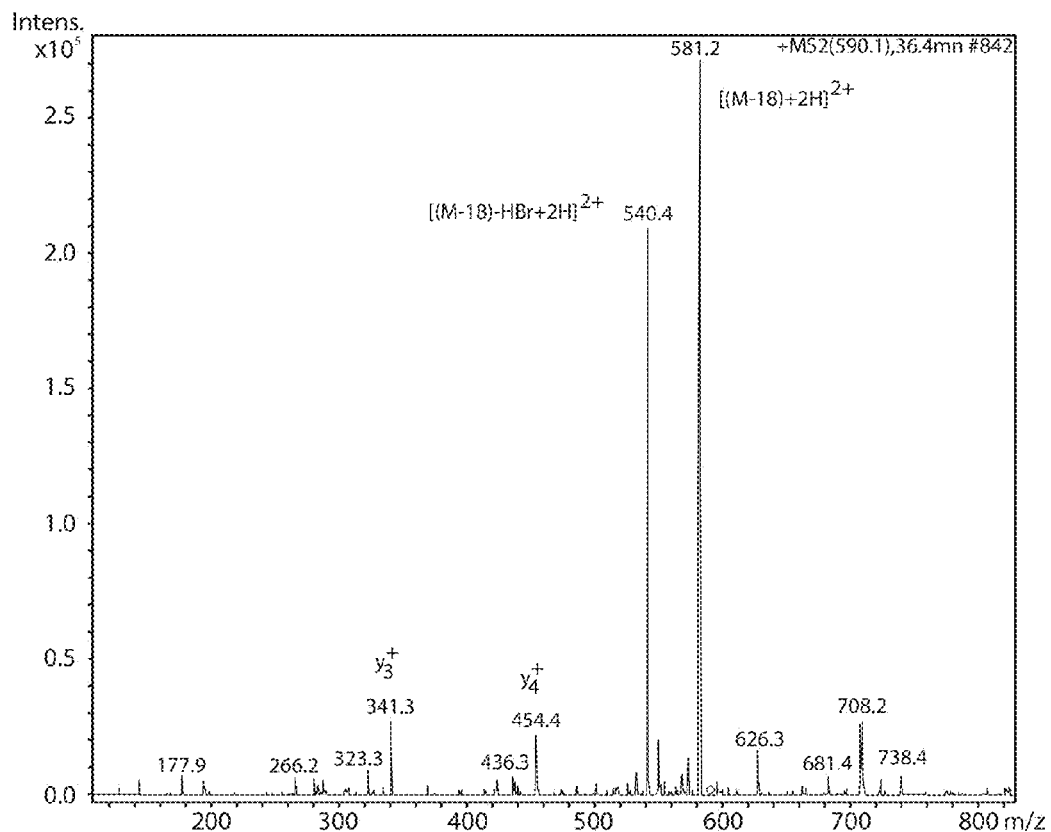
FIG. 6 is the E(BIBAF)GNILGHK MS/MS spectrum of 589 Da. The signal at 580 Da retains the characteristic isotopic pattern associated with the presence of bromine in a 2+ charge state, and is consistent with the doubly charged species resulting from the loss of water, $[M-18+2H]^{2+}$. Loss of water is a recognized low-energy fragmentation pathway for N-terminal glutamic acid peptides The isotopic pattern for the peak at 540 Da indicates a +2 charge absent bromine and is consistent with the loss of HBr from the side chain 4-(2'-bromoisobutyramido)phenylalanine

For further characterization of the incorporation of 1 into proteins in response to the amber codon, the most active RS was cloned into a pDule vector that contains one copy of Mj tRNA$_{CUA}$ to create pDule-BIBAF. Expression of GFP gene interrupted by an amber codon at site 134 in the presence of pDule-BIBAF was efficient and dependent on the presence of 1 (FIG. 1). Using 1 mM 1, 0.42 g of GFP-1 was purified per liter of media, while GFP-wt yielded 1.27 g/L under similar conditions (no GFP is produced in the absence of 1). To further demonstrate that 1 can be incorporated into recombinant proteins using pDule-BIBAF, we compared the masses of GFP-1 to GFP-wt using ESI-Q-T of mass analysis to verify that only a single 1 is incorporated in GFP (see FIGS. 4a and 4b). The site of incorporation of 1 into GFP was confirmed by analysis of the tandem mass spectrometry (MS/MS) fragmentation series of the relevant tryptic peptide (FIGS. 5a, 5b, and 6). Overall, the results of protein expression with affinity purification, SDS-PAGE, and MS analysis demonstrate the high fidelity and efficient incorporation of 1 at a genetically programmed site in GFP using pDule-BIBAF.

Figure 7A:
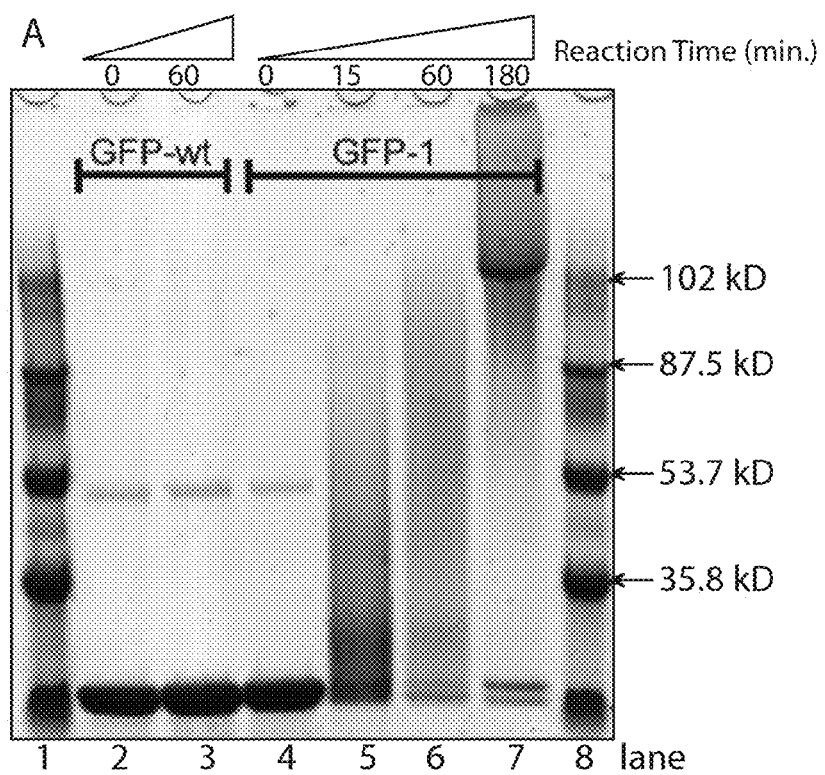
FIG. 7a is a characterization of ATRP grafting from GFP-wt and GFP-1 with $OEO_{300}MA$ monomer in PBS at 24° C. SDS-PAGE of crude time points (5 µg of protein was loaded on each lane of a 4-12% gel). The reaction produced no size change for GFP-wt (Lane 2 and 3), while the majority of GFP-1 showed significant size increases with increasing ATRP reaction time (Lane 4-7).
Figure 7B:
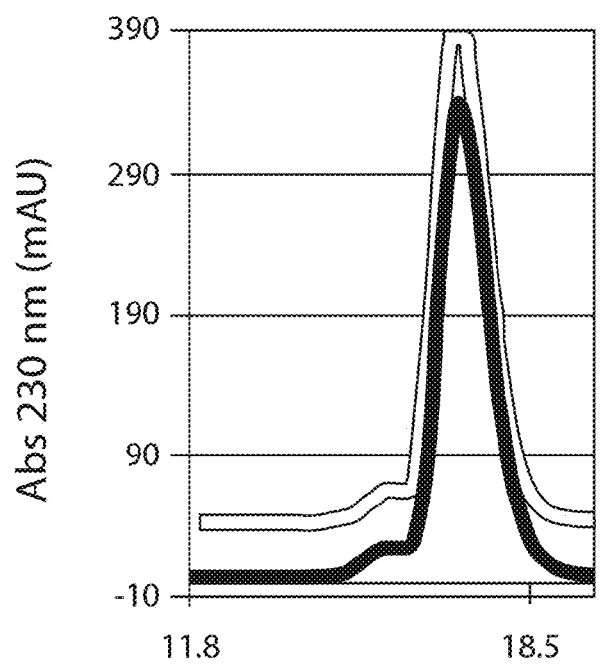
FIG. 7b is a SEC of GFP-wt. SEC of 0.1 mg of desalted reaction time-points on Superdex 200 at flow rate of 0.8 mL/min of PBS buffer monitored at 230 nm. GFP-wt eluted at the expected volume of 17.3 mL (black line) and was unaltered by the ATRP reaction (white line).
Figure 7C:
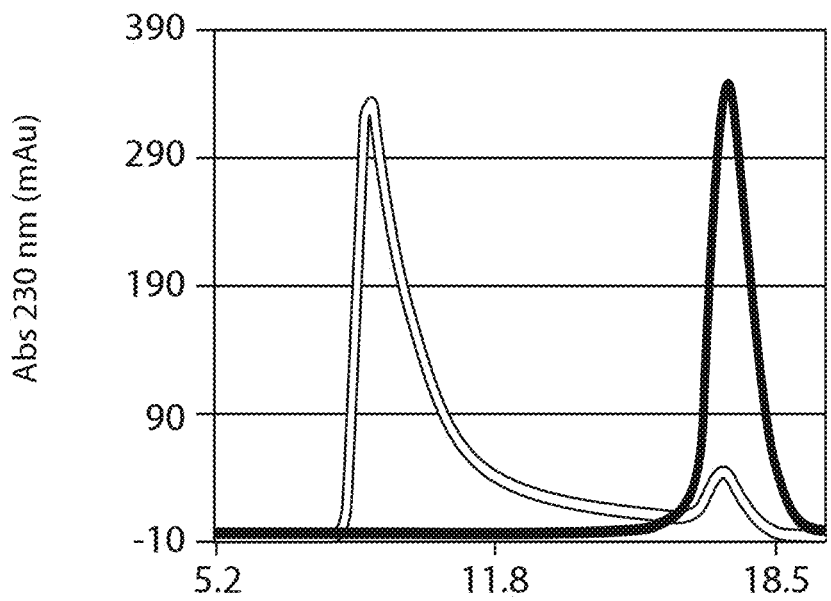
FIG. 7c is a SEC of GFP-1 ATRP. SEC of 0.1 mg of desalted reaction time-points on Superdex 200 at flow rate of 0.8 mL/min of PBS buffer monitored at 230 nm. SEC of GFP-1 ATRP reaction shows the protein significantly increasing in size. (black line, time=0; white line, time=180 min).
Figure 8:
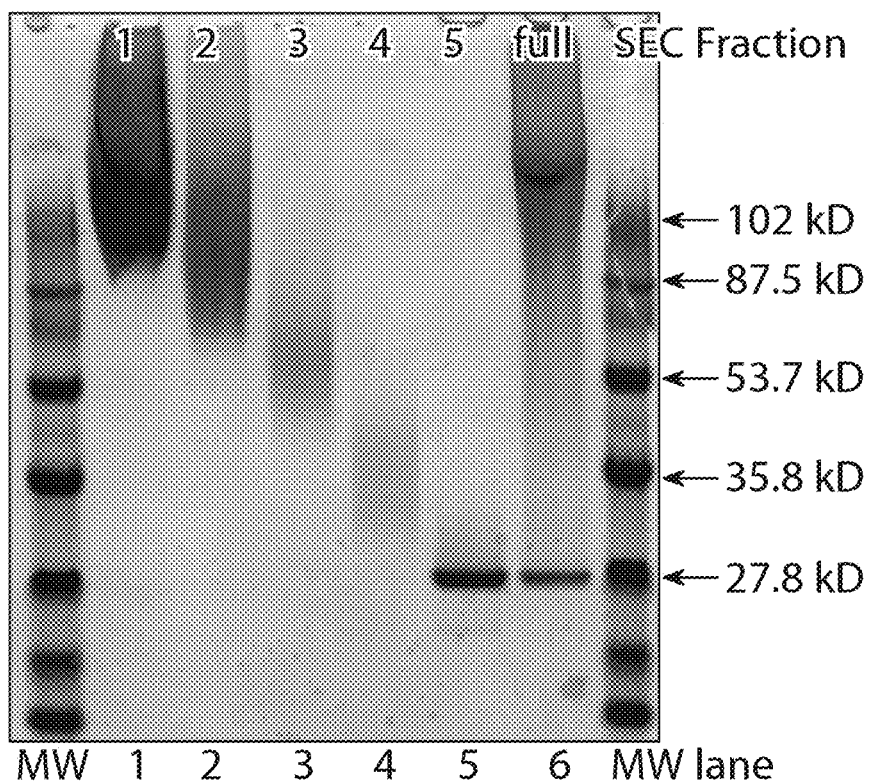
FIG. 8 is a SDS PAGE analysis of SEC fractionated ATRP reactions. ATRP reactions were separated by SEC, (FIG. 7c), and the individual fractions were concentrated and separated on a 4-12% gel and stained with Coomassie. The full 3 hr reaction mixture is in lane 6 and fractions 1-5 are in lanes 1-5 respectively. The GFP-polymer hybrid's change in size is due to polymer growth, as indicated by SEC and SDS-PAGE separation. Characterization of ATRP grafting from GFP-wt and GFP-1 with $OEO_{300}MA$ monomer in PBS at 24° C. (A) SDS-PAGE of crude time points (5 µg of protein was loaded on each lane of a 4-12% gel). The reaction produced no size change for GFP-wt (Lane 2 and 3), while the majority of GFP-1 showed significant size increases with increasing ATRP reaction time (Lane 4-7).

ATRP's tolerance of mild temperatures and aqueous conditions has been established for a variety of monomers in the presence of many biomolecules. The use of 1 as an initiator has never been reported. As polyMPEG-protein bioconjugates have shown efficient pharmacokinetics and therapeutic potency, OEO$_{300}$MA was selected as the monomer to demonstrate that the genetically incorporated initiator 1 can be used in an ATRP. The GFP-1 initiator and OEO$_{300}$MA monomer were degassed with nitrogen and the reaction was initiated by adding a degassed stock solution of 2,2'-bipyridine and Cu$^{+1}$/Cu$^{+2}$ (see Examples for details). The ATRP performed in degassed PBS buffer at 24° C. and samples were taken and quenched at different time points to assess polymer growth by SDS-PAGE and SEC (FIG. 7a and FIG. 7b). As expected, polymer growth from GFP-1 was evident by a shift of the signal from the conjugate to higher molecular weight (MW) with increasing ATRP reaction time, whereas no change was evident on GFP-wt under ATRP conditions. While ATRP is a radical-based method and can have early stage termination reactions leading to residual unreacted GFP-1, characterization with SEC showed that 93% of the GFP-1 initiator was incorporated into high MW polymers after 180 min (FIG. 7a, lane 7; FIG. 7c (white trace). Since the amide linkage connecting the polymer to GFP is very stable, this prevents separation via hydrolysis for analysis. Therefore, to verify that the polymers grown from the surface of GFP-1 did not significantly affect the structure of the protein, we compared fluorescence/protein concentration ratios, since GFP fluorescence intensity correlates with the structural integrity of the protein (see Example 8, Table 4) (Pedelacq et al., Nature Biotechnology 2006, 24, 79). To further characterize the polyMPEG-GFP bioconjugate, after 180 minutes the reaction was fractionated by SEC, yielding purified protein-polymers of different sizes. The fractionated soluble fluorescent polyMPEG-GFP samples exhibited the expected MW increase when characterized by SDS-PAGE (FIGS. 7c and 8).

Methods of producing a protein in a cell (e.g., a non-eukaryotic cell, such as an E. coli cell or the like, or a eukaryotic cell) with an initiator amino acid at a specified position are a feature of the invention. Proteins or polypeptides of interest having at least one initiator amino acid are a feature of the invention. Optionally, a protein of the invention may include a post-translational modification. In certain embodiments, the protein comprises an amino acid sequence that is at least 75% identical to that of a known protein, e.g., a therapeutic protein, a diagnostic protein, an industrial enzyme, or portion thereof.

Essentially any protein (or portion thereof) that includes an amino acid further comprising an initiator for a CRP, or that encodes multiple different unnatural amino acids (and any corresponding coding nucleic acid, e.g., which includes one or more selector codons) can be produced using the compositions and methods herein. No attempt is made to identify the hundreds of thousands of known proteins, any of which may be modified to include one or more unnatural amino acid, e.g., by tailoring any available mutation methods to include one or more appropriate selector codon in a relevant translation system. Common sequence repositories for known proteins include GenBank, EMBL, DDBJ, and the NCBI, among others. Typically, the proteins are, e.g., at least 60%, at least 70%, at least 75%, at least 80%, at least 90%, at least 95%, or at least 99% or more identical to any available protein (e.g., a therapeutic protein, a diagnostic protein, an industrial enzyme, or portion thereof, and the like), and they comprise one or more unnatural amino acid. Essentially any protein of interest can be modified to include an initiator comprising an unnatural amino acid.

Enzymes (e.g., industrial enzymes) or portions thereof with at least one initiator amino acid are also provided by the invention. Examples of enzymes include, but are not limited to, e.g., amidases, amino acid racemases, acylases, dehalogenases, dioxygenases, diarylpropane peroxidases, epimerases, epoxide hydrolases, esterases, isomerases, kinases, glucose isomerases, glycosidases, glycosyl transferases, haloperoxidases, monooxygenases (e.g., p450s), lipases, lignin peroxidases, nitrile hydratases, nitrilases, proteases, phosphatases, subtilisins, transaminase, and nucleases.

To make a protein that includes an initator amino acid, one may use host cells and organisms that are adapted for the in vivo incorporation of the initiator amino acid via orthogonal tRNA/RS pairs. Host cells are genetically engineered (e.g., transformed, transduced, or transfected) with one or more vectors that express the orthogonal tRNA, the orthogonal tRNA synthetase, and a vector that encodes the protein to be derivatized. Each of these components can be on the same vector, or each can be on a separate vector, or two components can be on one vector and the third component on a second vector. The vector can be, for example, in the form of a plasmid, a bacterium, a virus, a naked polynucleotide, or a conjugated polynucleotide.

The compositions of the invention and compositions made by the methods of the invention are optionally made in a cell. The O-tRNA/O-RS pairs or individual components of the invention may then be used in a host system's translation machinery, which results in an initiator amino acid being incorporated into a protein. For example, when an O-tRNA/O-RS pair is introduced into a host, e.g., *Escherichia coli*, the pair leads to the in vivo incorporation of an initiator amino acid, which can be exogenously added to the growth medium, into a protein, e.g., any protein where a polymer attachment is of interest, in response to a selector codon, e.g., an amber nonsense codon. Optionally, the compositions of the invention can be in an in vitro translation system, or in an in vivo system(s) with the initiator amino acid and may be used to facilitate production of a protein polymer hybrid.

Kits are also a feature of the invention. For example, a kit for producing a protein with an initator amino acid at a specified position is provided, where the kit includes a cell comprising an orthogonal tRNA that functions in the cell and recognizes a selector codon and an orthogonal aminoacyl-tRNA synthetase, packaged in one or more containers. In one class of embodiments, the kit further includes an initiator amino acid. In another class of embodiments, the kit further comprises instructional materials for producing the protein, an appropriate cell growth medium, reagents for introducing a target nucleic acid encoding the protein of interest and including the selector codon into the cell, or the like. Any composition, system or device of the invention can also be associated with appropriate packaging materials (e.g., containers, etc.) for production in kit form. A kit may also include a plasmid and instructions for practicing a method of the invention.

The above example illustrates the principle of genetic engineering of proteins to incorporate unnatural amino acids further comprising a single ATRP initiating site in a modified organism. Once proteins containing the unnatural amino acids containing additional functionality have been produced then it is possible to conduct a controlled polymerization using low concentrations of transition metal complex in the "grafting from" method from that specific site within the proteins. This procedure thereby permits exploitation of the synergistic power of functional protein-polymer conjugate materials in multiple biotherapy applications.

Using the method of this invention, one can obtain precisely modified proteins with a desired number of initiating groups in exact locations. The simple power of this method allows one to (a) form proteins that require no further modification, such as random attachment of initiating groups; (b) control the location of the initiating group so the polymer can be grown from one or more sites selected so that they can either be positioned to be totally free from the active site or are situated in ways to regulate active site activity; and (c) grow an exact number of well defined polymer chains with targeted molecular weight and site specific functionality from the protein. This method overcomes nearly all limitations of other previous methods to produce protein polymer hybrids.

While the method is exemplified by incorporating a radically transferable atom, an initiation functionality for any controlled radical polymerization process can be introduced into nearly any protein thereby providing the ability to advance the field of protein polymer hybrids from the current class of non-functional proteins, e.g. bovine serum albumin, towards enzymes or therapeutically relevant systems. Therefore this invention allows one to assay the efficacy of the system and properly study the effects of polymer placement using commercially available enzyme assays.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. One of skill in the art will appreciate that the invention is not limited to those exact sequences, e.g., as in the Examples and sequence listing. One of skill will appreciate that the invention also provides, e.g., many related and unrelated sequences with the functions described herein, e.g., encoding an appropriate O-tRNA or an O-RS. The invention is further illustrated by the foregoing examples, which should not be construed as further limiting.

EXAMPLES

Example 1

N-Boc-4-(2'-bromoisobutyramido)phenylalanine

Commercially available N-Boc 4-aminophenylalanine (3.62 g, 0.01447 mol) was dissolved in 50 mL of dry THF. 2-bromoisobutyryl bromide (1.757 mL, 0.01422 mol) was added dropwise over 30-60 seconds with vigorous stirring. The reaction was complete after 10 min (monitored by TLC). After approximately 20 min. the entire reaction mixture (including newly formed precipitate) was transferred to a separatory funnel with $CHCl_3$, and approximately 100 mL of $H_2O$. The reaction mixture was extracted with $CHCl_3$ (3×50 mL). The organic phase was washed with distilled water (2×50 mL) and brine (50 mL). The organic phase was dried with $MgSO_4$ and evaporated in vacuo to obtain the crude product (4.55 g). The crude solid product was recrystallized in 20-30 mL acetonitrile three times to purify the product. After three recrystallizations, N-Boc-4-(2'-bromoisobutyramido)phenylalanine was obtained in 65% yield (3.63 g). $^1$H NMR (500 MHz, DMSO): $\delta$9.4 (s, 1H, COOH), $\delta$7.8 (s, 1H, NH), $\delta$7.5 (d, 2H, Ar H), $\delta$7.1 (d, 2H, Ar H), $\delta$6.0 (d, 1H, NH), $\delta$4.2 (d, 1H, CH), $\delta$3.05 (dd, 2H, $CH_2$), $\delta$2.0 (s, 6H, $CH_3$), $\delta$1.3 (s, 9H, $CH_3$).

Example 2

4-(2'-bromoisobutyramido)phenylalanine

N-Boc-4-(2'-bromoisobutyramido)-phenylalanine (4.8 g, 0.0112 mol) was dissolved in 50 mL ethyl acetate under argon and dry 4 M HCl in dioxane (50 mL) was subsequently added to the solution while stirring at room temperature overnight. The reaction mixture was then evaporated under reduced pressure to a final volume of 5-10 mL. Pentane was then added to the solution, and the precipitate was filtered using an M type filter crucible and dried under reduced pressure. 4-(2'-bromoisobutyramido)phenylalanine hydrochloride was obtained in 97% yield (3.93 g). $^1$H NMR (500 MHz, DMSO): $\delta$9.8 (s, 1H, COOH), $\delta$8.4 (s, 1H, NH), $\delta$7.6 (d, 2H, Ar H), $\delta$7.2 (d, 2H, Ar H). $\delta$4.1 (bs, 1H, CH), $\delta$3.1 (d, 2H, $CH_2$), $\delta$2.0 (s, 6H, $CH_3$). $^{13}$C NMR (500 MHz, DMSO): $\delta$171.0 (1C), $\delta$170.0 (1C), $\delta$138.5 (1C), $\delta$130.9 (1C), $\delta$130.3 (2C), $\delta$121.2 (2C), $\delta$67.0 (dioxane), $\delta$61.5 (1C), $\delta$53.9 (1C), $\delta$35.8 (1C), $\delta$31.5.0 (2C). FT-IR($CH_3CN$) $v_{max}$ cm$^{-1}$ 3374, 2977, 1740, 1664, 1600, 1522, 1416, 1112, 840, 529. LCMS m/z for $C_{13}H_{17}BrN_2O_3$ [M+H]$^+$: 330.19. found: 329.3 and 331.2. HRMS calculated 329.0501. found 329.0507 (i-Fit 0.7).

Example 3

Selection of an Aminoacyl-tRNA Synthetase Specific for
4-(2'-Bromoisobutyramido)Phenylalanine The library of aminoacyl-tRNA synthetases was encoded on a kanamycin (Kn) resistant plasmid (pBK, 3000 bp) under control of the constitutive *Escherichia coli* GlnRS promoter and terminator. The aminoacyl synthetase library (3D-Lib) was randomized as follows: Leu65, His70, Gln155, and Ile159 were randomized to all 20 natural amino acids; Tyr32 was randomized to 15 natural amino acids (less Trp, Phe, Tyr, Cys, and Ile); Asp158 was restricted to Gly, Ser, or Val; Leu162 was restricted to Lys, Ser, Leu, His, and Glu; and Phe108 and Gln109 were restricted to the pairs Trp-Met, Ala-Asp, Ser-Lys, Arg-Glu, Arg-Pro, Ser-His, or Phe-Gln. The library plasmid, pBK-3D-Lib, was moved between cells containing a positive selection plasmid (pCG) and cells containing a negative selection plasmid (pNEG).

The positive selection plasmid, pCG (10000 bp), encodes a mutant *Methanococcus jannaschii* (Mj) tyrosyl-tRNA$_{CUA}$, an amber codon-disrupted chloramphenicol acetyltransferase, an amber codon-disrupted T7 RNA polymerase that drives the production of green fluorescent protein, and the tetracycline (Tet) resistance marker. The negative selection plasmid, pNEG (7000 bp), encodes the mutant tyrosyl-tRNA$_{CUA}$, an amber codon-disrupted barnase gene under control of an arabinose promoter and rrnC terminator, and the ampicillin (Amp) resistance marker. pCG electrocompetent cells and pNEG electrocompetent cells were made from DH10B cells carrying the respective plasmids and stored in 100 µL aliquots at −80° C. for future rounds of selection.

The synthetase library in pBK-3D-Lib was transformed by electroporation into DH10B cells containing the positive selection plasmid, pCG. The resulting pCG/pBK-3D-Lib-containing cells were amplified in 1 L of 2×YT with 50 µg/mL Kn and 25 µg/mL Tet with shaking at 37° C. The cells were grown to saturation, then pelleted at 5525 rcf, resuspended in 30 mL of 2×YT and 7.5 mL of 80% glycerol, and stored at −80° C. in 1 mL aliquots for use in the first round of selections.

For the first positive selection, 2 mL of pCG/pBK-3D-Lib cells were thawed on ice before addition to 1.2 L of room temperature 2×YT media containing 50 µg/mL Kn and 25 µg/mL Tet. After incubation (11 h, 250 rpm, 37° C.), a 200 µL aliquot of these cells was plated on eleven 15 cm GMML-agar plates containing 50 µg/mL Kn, 25 µg/mL Tet, and 60 µg/mL chloramphenicol (Cm). The positive selection agar medium also contained 1 mM 4-(2'-bromoisobutyramido)phenylalanine hydrochloride. After spreading, the surface of the plates was allowed to dry completely before incubation (37° C., 15 h). To harvest the surviving library members from the plates, 10 mL of 2×YT (50 µg/mL Kn, 25 µg/mL Tet) was added to each plate. Colonies were scraped from the plate using a glass spreader. The resulting solution was incubated with shaking (60 min, 37° C.) to wash cells free of agar. The cells were then pelleted, and plasmid DNA was extracted. For the first positive selection a Qiagen midiprep kit was used to purify the plasmid DNA. For all other plasmid purification steps a Qiagen miniprep kit was used to purify the plasmid DNA. The smaller pBK-3D-Lib plasmid was separated from the larger pCG plasmid by agarose gel electrophoresis and extracted from the gel using the Qiagen gel extraction kit.

The purified pBK-3D-Lib was then transformed into pNEG-containing DH10B cells. A 100 µL sample of pNEG electrocompetent cells was transformed with 50 ng of purified pBK-3D-Lib DNA. Cells were rescued in 1 mL of SOC for 1 h (37° C., 250 rpm) and the entire 1 mL of rescue solution was plated on three 15 cm LB plates containing 100 µg/mL Amp, 50 µg/mL Kn, and 0.2% L-arabinose. Cells were collected from plates and pBK-3D-Lib plasmid DNA was isolated in the same manner as described above for positive selections.

For the second round of positive selection, 50 ng of purified library DNA was transformed into 100 µL of pCG competent cells. The transformants were rescued for 1.5 h in 1 mL of SOC (37° C., 250 rpm). A 50 µL sample of these cells was plated on three plates prepared as described in the first positive selection on LB agar plates.

For the second negative selection, one plate was spread with 250 µL of rescued cells, and two plates were spread with 50 µL of rescued cells and then incubated (12-16 h, 37° C.). For this round, the cells were plated on LB agar containing 100 µg/mL Amp, 50 µg/mL Kn, and 0.04% L-arabinose.

In order to evaluate the success of the selections based on variation in synthetase efficacy (as opposed to traditional survival/death results), the synthetases resulting from the selection rounds were tested with the pALS plasmid. This plasmid contains the sfGFP reporter with a TAG codon at residue 150 as well as tyrosyl-tRNA$_{CUA}$. When a pBK plasmid with a functional synthetase is transformed with the pALS plasmid and the cells are grown in the presence of the appropriate amino acid on autoinduction agar, sfGFP is expressed and the colonies are visibly green.

One microliter of each library resulting from the second positive and the second negative rounds of selection was transformed with 60 µL of pALS-containing DH10B cells. The cells were rescued for 1 hr in 1 mL of SOC (37° C., 250 rpm). A 250 µL and 50 µL of cells from each library were plated on autoinducing minimal media with 25 µg/mL Kn, 25 µg/mL Tet, and 1 mM 4-(2'-bromoisobutyramido)phenylalanine hydrochloride. Plates were grown at 37° C. for 24 hours and then grown on the bench top, at room temperature, for an additional 24 hours.

Autoinducing agar plates were prepared by combining the reagents in Table 1, column A with an autoclaved solution of 40 g of agarose in 400 mL water. Sterile water was added to a final volume of 500 mL. Antibiotics were added to a final concentration of 25 µg/mL Tet and 25 µg/mL Kan. Nine plates were poured with 1 mM 4-(2'-bromoisobutyramido)phenylalanine hydrochloride, and nine plates were maintained as controls without UAA.

A total of 92 visually green colonies were selected from the two 1 mM 4-(2'-bromoisobutyramido)phenylalanine hydrochloride plates and used to inoculate a 96-well plate containing 0.5 mL per well non-inducing minimal media (Table 2, column B, with sterile water added to a final volume of 500 mL) with 25 µg/mL Kn, 25 µg/mL Tet. After 24 hours of growth (37° C., 250 rpm), 5 µL of these non-inducing samples were used to inoculate 96-well plates with 0.5 mL autoinduction media (Table 2, column C, with sterile water added to a final volume of 500 mL) containing 25 µg/mL Kn, 25 µg/mL Tet with and without 1 mM 4-(2'-bromoisobutyramido)phenylalanine hydrochloride. Fluorescence measurements of the cultures were collected 40 hours after inoculation using a HORIBA Jobin Yvon FluoroMax®-4. The emission from 500 to 520 nm (1 nm bandwidth) was summed with excitation at 488 nm (1 nm bandwidth). Samples were prepared by diluting suspended cells directly from culture 100-fold with phosphate buffer saline (PBS).

Fluorescence measurements of 92 synthetases with GFP clones were conducted. Expressions of 500 µL were grown for 40 hours before dilution of suspended cells directly from culture 100-fold with phosphate buffer saline (PBS). Fluorescence measurements were collected using a HORIBA Jobin Yvon FluoroMax®-4. The emission from 500 to 520 nm (1 nm bandwidth) was summed with excitation at 488 nm (1 nm bandwidth). See FIG. 2.

TABLE 2

Components for autoinducing and non-inducing mediums, for final volume of 500 mL.

|  | A Autoinduction medium | B Non-inducing medium | C Autoinducing plates |
|---|---|---|---|
| 5% aspartate, pH 7.5 | 25 mL | 25 mL | 25 mL |
| 10% glycerol | 25 mL | — | 25 mL |
| 25x 18 amino acid mix | 20 mL | 20 mL | 20 mL |
| 50x M | 10 mL | 10 mL | 10 mL |
| leucine (4 mg/mL), pH 7.5 | 5 mL | 5 mL | 5 mL |
| 20% arabinose | 1.25 mL | — | 1.25 mL |
| 1M MgSO$_4$ | 1 mL | 1 mL | 1 mL |
| 40% glucose | 625 μL | 6.25 mL | 125 μL |
| Trace metals | 100 μL | 100 μL | 100 μL |

Example 4

Fluorescence Analysis of Highest-Fluorescing Clones

Figure 3:
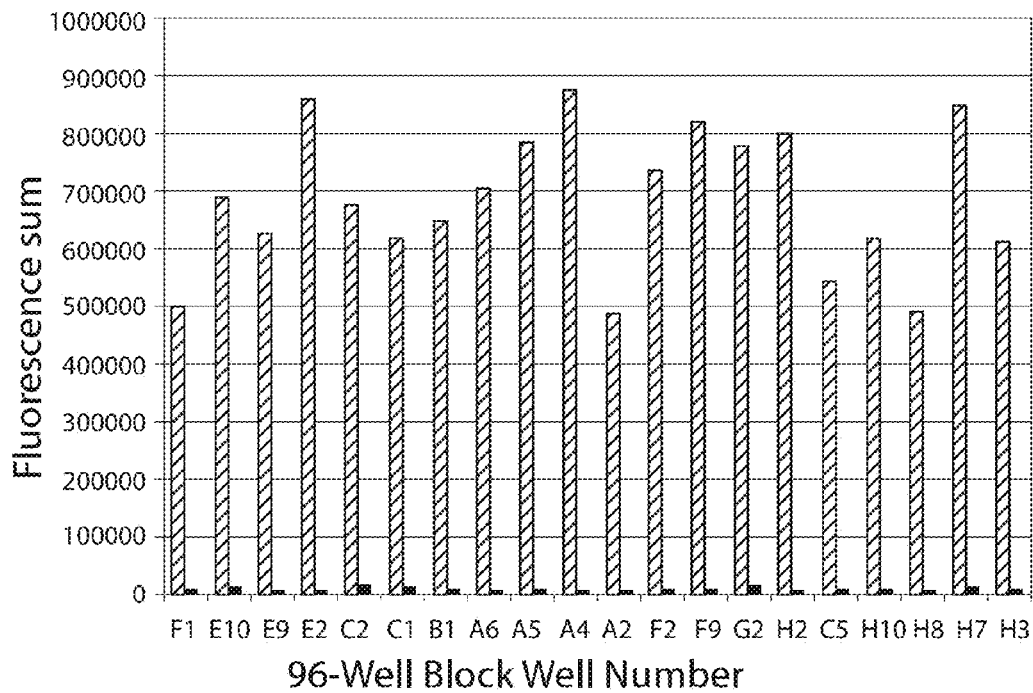
FIG. 3 shows the fluorescence measurements of 20 highest-expressing synthetases with GFP clones. The striped bar lines represent colonies induced in media containing 1 mM 1 while the solid lines represent colonies induced in the absence of UAA. Expressions of 3 mL were grown for 40 hours before dilution of suspended cells directly from culture 100-fold with phosphate buffer saline (PBS). Fluorescence measurements were collected using a HORIBA Jobin Yvon Fluoro-Max®-4. The emission from 500 to 520 nm (1 nm bandwidth) was summed with excitation at 488 nm (1 nm bandwidth).

Non-inducing cultures (3 mL) with 25 μg/mL Kn and 25 μg/mL Tet were grown to saturation (37° C. with shaking at 250 rpm) from the 20 highest-fluorescing colonies. Autoinduction cultures (3 mL) with 25 μg/mL Kn and 25 μg/mL Tet were inoculated with 30 μL of non-inducing cultures and grown with and without 1 mM 1 at 37° C. with shaking at 250 rpm. After approximately 40 hours, fluorescence was assessed (see FIG. 3). The top eight performing clones were sequence revealing five unique members (Table 3). The top performing clone (G2) was moved from the pBK-G2 plasmid to the pDule plasmid (pDule-BIBAF). pDule plasmid was generated by amplifying the MjYRS gene from the pBK plasmid isolated from the library using primers RSmovef (5'-CGCGCGCCATGGACGAATTTGAAATG-3') and RSmover (5'-GACTCAGTCTAGGTAC-CCGTTTGAAACTGCAGTTATA-3'). The amplified DNA fragments were cloned in to the respective sites on the pDule plasmids using the incorporated NcoI and KpnI sites.

TABLE 3

Amino acid sequences for synthetase library members

|  | 32 | 65 | 108 | 109 | 158 | 159 |
|---|---|---|---|---|---|---|
| A4 | Gly | Glu | Phe | Gln | Gly | Val |
| F9 | Gly | Glu | Phe | Gln | Gly | Cys |
| G2 | Gly | Glu | Trp | Met | Ser | Ile |
| H2 | Gly | Glu | Phe | Gln | Gly | Leu |
| H7 | Gly | Glu | Phe | Gln | Gly | Asn |
| Native | Tyr | Leu | Phe | Gln | Asp | Ile |

Example 5

Expression and Purification of GFP-1

DH10B *E. coli* cells co-transformed with the pBad-sfGFP-134TAG vector and the machinery plasmid pDule-BIBAF were used to inoculate 5 mL of non-inducing medium containing 100 μg/mL Amp and 25 μg/mL Tet. The non-inducing medium culture was grown to saturation with shaking at 37° C., and 5.0 mL was used to inoculate 0.5 L autoinduction medium with 100 μg/mL Amp, 25 μg/mL Tet, and 1 mM 4-(2'-bromoisobutyramido)phenylalanine hydrochloride (0.5 L of media grown in 2 L plastic baffled flasks). After 40 hours of shaking at 37° C., cells were collected by centrifugation.

The protein was purified using BD-TALON cobalt ion-exchange chromatography. The cell pellet was resuspended in wash buffer (50 mM sodium phosphate, 300 mM sodium chloride, pH 7) containing 1 mg/mL chicken egg white lysozyme, and sonicated 3×1 min while cooled on ice. The lysate was clarified by centrifugation, applied to 6-9 mL bed-volume resin, and bound for 30 min. Bound resin was washed with >50 volumes wash buffer. The protein was eluted from the bound resin with 2.5 mL aliquots of elution buffer (50 mM sodium phosphate, 300 mM sodium chloride, 150 mM imidazole pH 7) until the resin turned pink and the color of the eluent the column was no longer green. The elusions concentrations were check with a Bradford protein assay. The protein was desalted into PBS using PD10 columns and concentrated with 3000 MWCO centrifuge filters.

The location of incorporation of 1 at site D134 in GFP protein is indicated by the space-filling amino acid (previously Asp-134) represented in FIG. 9 as a blackened mass at the bottom of GFP-1. Altering the amino acid at site 134 in a flexible loop unconnected to the chromophore does not affect the stability or fluorescence of GFP.

Example 6

MS Analysis of GFP-1

All protein samples processed for MS analysis were the same proteins used in the subsequent ATRP reactions. The samples in 50 mM Na H$_2$PO$_4$ pH 6.5 were exchanged into 20 mM ammonium acetate buffer pH 7 using PD10 gel filtration columns. Proteins in 20 mM ammonium acetate buffer were dried overnight on a vacuum-line. Protein samples for full protein mass spectrometry were resuspended in 1:1 water: acetonitrile with 0.2% formic acid. The samples were analyzed at the Mass Spectrometry Facility at University of Illinois Urbana-Champaign under the direction of Dr. Furong Sun using their ESI-Q-T of Ultima (see FIGS. 4a and 4b).

Trypsin digestion of GFP and GFP-1 were performed using Trypsin In-Gel Digest Kit from Sigma Aldrich (PP0100). Mass spectral analyses were performed on an Agilent 1100 series LC/MSD SL ion trap mass spectrometer with electrospray ionization and MS/MS capabilities. Ten microliters of the protein digests were injected onto a Zorbax 300SB-C8 column (narrow-bore 2.1×150 mm 5-micron) for separation using a gradient of 5-95% CH$_3$CN (with 0.1% formic acid) in water (with 0.1% formic acid) over 75 min (5-25% 0-40 minutes, 25-95% 40-60 minutes, 95-5% 60-75 minutes). The flow rate was set to 0.25 mL/min. The SL Trap MS was operated in the SPS mode under the normal scan setting. The dry temperature was 325° C., with dry gas flow of 10.0 L/min and a nebulizer pressure of 40 psi. For the MS/MS experiments, the instrument was operated in the auto MS/MS mode selecting two precursor ions with preference given to doubly charged ions while singly charged ions were excluded.

The peptide of interest, E(BIBAF)GNILGHK (C$_{50}$H$_{77}$N$_{14}$O$_{14}$Br, Exact Mass=1176.49 Da) generated a [M+2H]$^{2+}$ peak at 589.2 Da. An extracted ion chromatograph of mass 589 showed a single peak eluting at 36.3 minutes containing an isotopic cluster with a unique pattern consistent with that expected for the bromine containing peptide. The observed and predicted isotopic abundance patterns compare favorably (see FIGS. 5a and 5b). MS/MS analysis of the peptide at 589 Da further confirmed incorporation of the bromine into the peptide (see FIG. 6).

Example 7

ATRP Reactions Grafting from GFP-wt and GFP-1

Initiator stock solution: Bpy (16.70 mg, 1.07*10$^{-3}$ mmol) and Cu(II)Br$_2$ (6 mg, 2.68*10$^{-4}$ mmol) were dissolved in 10 mL of H$_2$O; the solution was deoxygenated with nitrogen. Cu(I)Br (3.8 mg, 2.68*10$^{-4}$ mmol) was added to the mixture.
GFP-wt, 0 and 3 hr ATRP Reaction Monomer, OEO$_{300}$MA (21 mg, 6.9*10$^{-2}$ mmol) was added to 100 µL of GFP-wt (10.2 mg, 3.4*10$^{-2}$ mmol). This solution was deoxygenated with nitrogen for 20 min. and then degassed initiator solution (250 µl) was added to the reaction mixture. The zero time sample was removed and the reaction was sealed and mixed for 3 hours then quenched by exposure to air.

GFP-1, 0 and 3 hr ATRP Reaction

Monomer, OEO$_{300}$MA (10 mg, 3.42*10$^{-2}$ mmol) was added to 100 µL of GFP-1 (6 mg, 2.14*10$^{-4}$ mmol). This solution was deoxygenated with nitrogen for 20 min. then degassed initiator solution (100 µL) was added to the reaction mixture. The reaction was sealed and mixed for 3 hours then quenched by exposure to air.

Example 8

Characterization of Conjugates Formed by ATRP Grafting from GFP-wt and GFP-1

All reactions were diluted to 3 mL with PBS and concentrated to 300 µL using a 3000 MWCO centrifuge filter. This process was repeated 3 times for each reaction to insure that all monomer, copper and ligand was removed. All reactions were then diluted to 1.0 mg protein/mL PBS after protein concentration was assessed using BCA protein assay. Crude samples (5 µg) from each reaction were analyzed by SDS-PAGE. A 4-12% gel was run at 150 V and was stained with Coomassie blue.

To verify that the polymers grown from the surface of GFP-1 did not significantly affect the structure of the protein, fluorescence/protein concentration ratios were compared. All of the reactions were diluted to 1.0±0.1 mg/mL based on a BCA protein assay. Fluorescence measurements were collected using a HORIBA Jobin Yvon FluoroMax®-4. The emission from 500 to 520 nm (1 nm bandwidth) was summed with excitation at 488 nm (1 nm bandwidth). Samples were prepared by diluting 100-fold with PBS. Results of fluorescence measurements are shown in Table 4.

TABLE 4

Fluorescent measurements of GFP and GFP-polymer hybrids

| ATRP Reaction | GFP Fluorescent |
| --- | --- |
| GFP-wt, 0 hr | 7.6 × 10$^6$ |
| GFP-wt, 3 hr | 8.6 × 10$^6$ |
| GFP-1, 0 hr | 7.2 × 10$^6$ |
| GFP-1, 3 hr | 8.1 × 10$^6$ |

For SEC analysis 0.1 mg of each reaction was separated on a Superdex 200 SEC column at a flow rate of 0.8 mL/min in PBS. The samples were monitored at 230 nm and 280 nm (FIGS. 7a, 7b, and 7c). Five major fractions were collected from the SEC separation and concentrated for analysis by SDS-PAGE (FIG. 8). This data clearly show that polymer chains were grown from the 2-bromoisobutyryl functionality incorporated into GFP-1 by genetic incorporation of the unnatural amino acid 1.

In light of the general disclosure provided herein above, with respect to the manner of practicing this inventive method, those skilled in the art will appreciate that this disclosure enables the practice of the inventive method according to the aspects and embodiments disclosed above. The experimental details are provided to ensure a complete written description of this invention, including the best mode thereof. However, it will be appreciated that the scope of this invention should not be construed in terms of the specific examples provided. Rather, the scope of this invention is to be apprehended with reference to the claims appended hereto, in light of the complete description of this inventive method constituted by this entire disclosure.

It is to be understood that the present invention may have various other embodiments. Furthermore, while the form of the invention herein shown and described constitute embodiments of the invention, it is not intended to illustrate all possible forms thereof. It will also be understood that the words used are words of description rather than limitation, and that various changes may be made without departing from the spirit and scope of the invention disclosed. The scope of the invention should not be limited solely to the examples given.

What is claimed is:

1. A compound according to Formula 6:

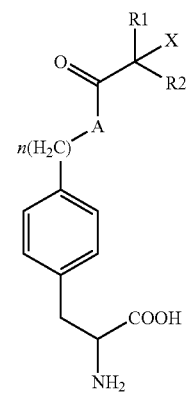

6 wherein R1 is H, C1-C8 alkyl, cycloalkyl, heterocycloalkyl, aryl, or heteroaryl; R2 is C1-C8 alkyl, cycloalkyl, heterocycloalkyl, aryl, or heteroaryl; X is F, Cl, Br, I, N$_3$, alkoxyamine, or a thiocarbonyl thio moiety; A is O, S, or NR, wherein R is H, C1-C8 alkyl, cycloalkyl, heterocycloalkyl, aryl, or heteroaryl; and n is 0, 1, 2, or 3; or a salt thereof.

2. The compound of claim 1, as described by formula 6, wherein R1 is H, methyl, or phenyl; R2 is methyl, or phenyl; X is F, Cl, Br, I; or N$_3$; A is O, S, or NR, wherein R is H, methyl, or phenyl; n is 1; or a salt thereof.

3. The compound of claim 1, according to formula 7:

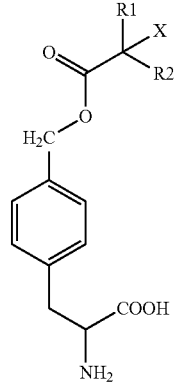

7 wherein R1 and R2 are independently H, methyl, or phenyl; X is F, Cl, Br, I; or N$_3$;
or a salt thereof.

4. The compound of claim 3, according to Formula 7b:

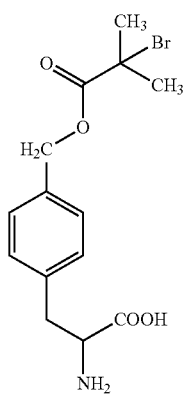

7b or a salt thereof.

5. The compound of claim 3, according to Formula 7c:

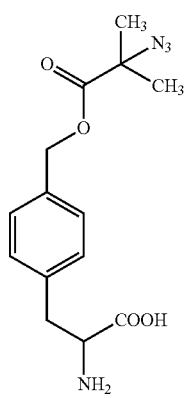

7c or a salt thereof.

6. The compound of claim 1, wherein R1 and R2 are independently H, methyl, or phenyl; X is F, Cl, Br, I, or N$_3$; A is O, S, or NR, wherein R is H, methyl, or phenyl; n is 0; or a salt thereof.

7. The compound of claim 6, according to formula 8:

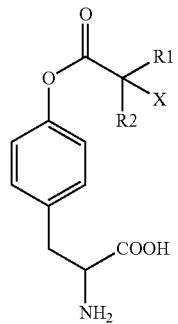

8 wherein R1 and R2 are independently H, methyl, or phenyl; X is F, Cl, Br, I, or N$_3$;
or a salt thereof.

8. The compound of claim 7, according to formula 8b:

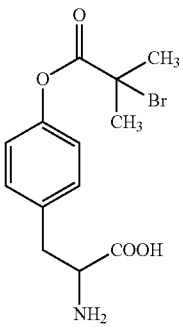

8b or a salt thereof.

9. The compound of claim 7, according to formula 8c:

8c or a salt thereof.

10. The compound of claim 6, according to formula 9,

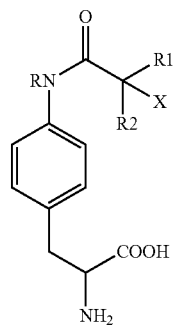

9 wherein R1 and R2 are independently H, methyl, or phenyl; X is F, Cl, Br, I, or N$_3$; R is H, methyl, or phenyl;
or a salt thereof.

11. The compound of claim 10, according to formula I:

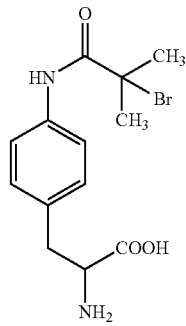

1 or a salt thereof.

12. The compound of claim 10, according to formula 1b:

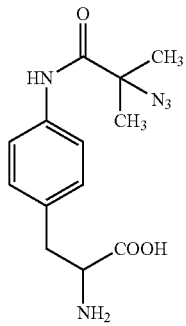

1b or a salt thereof.

13. A method of preparing a compound of formula 6, comprising the steps of
   (a) providing an N-Boc-protected tyrosine derivative of formula 4,

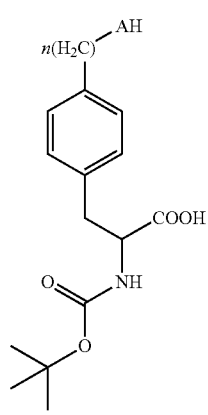

4

(b) reacting said derivative of formula 4 with an acyl halide of formula 10,

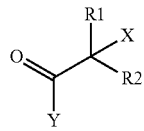

10 optionally in the presence of a base, to produce an N-Boc-protected intermediate of formula 5,

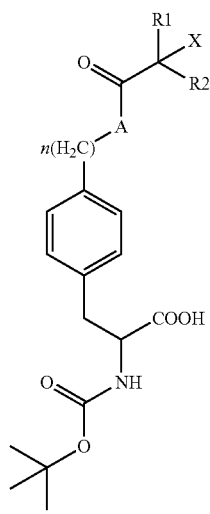

5

(c) deprotecting said intermediate of formula 5 to form salt compound of formula 6a,

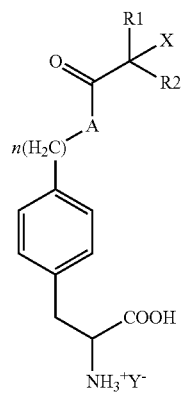

6a and (d) neutralizing said salt compound with base to produce the compound represented by formula 6,

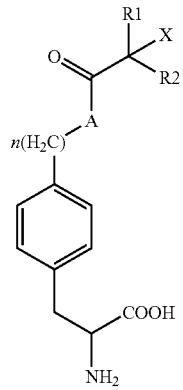

6 wherein R1 and R2 are independently H, C1-C8 alkyl, cycloalkyl, heterocycloalkyl, aryl, or heteroaryl; X is F, Cl, Br, I, $N_3$, alkoxyamine, or a thiocarbonyl thio moiety; Y is F, Cl, Br, I, or trifluoroacetate; A is O, S, or NR, wherein R is H, C1-C8 alkyl, cycloalkyl, heterocycloalkyl, aryl, or heteroaryl; n is 0, 1, 2, or 3; or a salt thereof.

14. The method of claim 13, wherein R1 and R2 are independently H, methyl, or phenyl; X is F, Cl, Br, I, or $N_3$; Y is F, Cl, Br, I, or trifluoroacetate; A is O, S, or NR, wherein R is H, methyl, or phenyl; and n is 1.

15. The method of claim 14, wherein R1 and R2 are independently H, methyl, or phenyl; X is Br or $N_3$; Y is Cl or Br; A is O or NH.

16. The method of claim 14, wherein R1 and R2 are independently H, methyl, or phenyl; X is Br; Y is Cl or Br; A is O or NH.

17. The method of claim 14, wherein R1 and R2 are independently H, methyl, or phenyl; X is $N_3$; Y is Cl or Br; A is O or NH.

18. The method of claim 13, wherein R1 and R2 are independently H, methyl, or phenyl; X is F, Cl, Br, I, or $N_3$; Y is F, Cl, Br, I, or trifluoroacetate; A is O, S, or NR, wherein R is H, methyl, or phenyl; and n is 0.

19. The method of claim 18, wherein R1 and R2 are independently H, methyl, or phenyl; X is Br; Y is Cl or Br; A is O or NH.

20. The method of claim 18, wherein R1 and R2 are independently H, methyl, or phenyl; X is $N_3$; Y is Cl or Br; A is O or NH.

21. The method of claim 13, wherein said deprotecting is accomplished by treating a compound of formula 5 with a solution containing hydrogen chloride or trifluoroacetic acid.

* * * * *